(12) United States Patent
Higgins et al.

(10) Patent No.: US 7,951,405 B2
(45) Date of Patent: May 31, 2011

(54) COMBINED TREATMENT WITH CISPLATIN AND AN EPIDERMAL GROWTH FACTOR RECEPTOR KINASE INHIBITOR

(75) Inventors: Brian Higgins, Nutley, NJ (US); Kenneth Kolinsky, Nutley, NJ (US)

(73) Assignee: OSI Pharmaceuticals, LLC, Farmingdale, NY (US)

( * ) Notice: Subject to any disclaimer, the term of this patent is extended or adjusted under 35 U.S.C. 154(b) by 615 days.

(21) Appl. No.: 11/145,495

(22) Filed: Jun. 3, 2005

(65) Prior Publication Data

US 2005/0271747 A1 Dec. 8, 2005

Related U.S. Application Data

(60) Provisional application No. 60/576,790, filed on Jun. 3, 2004.

(51) Int. Cl.
*A61K 33/24* (2006.01)
*A61K 31/517* (2006.01)

(52) U.S. Cl. .................................... 424/649; 514/266.2
(58) Field of Classification Search .................. None
See application file for complete search history.

(56) References Cited

U.S. PATENT DOCUMENTS

| 2002/0076408 A1 | 6/2002 | Buchsbaum | 424/145.1 |
| 2003/0108545 A1 | 6/2003 | Rockwell et al. | 424/143.1 |
| 2003/0157104 A1 | 8/2003 | Waksal | 424/145.1 |

FOREIGN PATENT DOCUMENTS

| WO | 9843646 A1 | 10/1998 |
| WO | WO 99/60023 | 11/1999 |
| WO | WO 01/12227 | 2/2001 |
| WO | WO 01/34574 | 5/2001 |
| WO | WO 01/76586 | 10/2001 |
| WO | WO 02/055106 | 12/2001 |
| WO | WO 02/05791 | 1/2002 |
| WO | WO 02/39121 A | 5/2002 |
| WO | WO 02/45653 A | 6/2002 |
| WO | WO 02/089842 | 11/2002 |
| WO | WO 03/088971 | 10/2003 |
| WO | WO 2004/014386 A | 2/2004 |
| WO | WO 2005/018677 | 3/2005 |

OTHER PUBLICATIONS

Scagliotti (Supplement Di Tumori: Official Journal of Societa Italiana Di Cancerologia, 2002, vol. 1, pp. S34-S36).*
Herbst (Seminars in Oncology, Jun. 2003, vol. 30, No. 3, Suppl. 7, pp. 34-36).*
Drug Facts and Comparisons@, 1999 Edition, Kastrup et al, Ed.s, pp. 3282, 3338-3339 and 3447.*
Abstract of Plunkett et al, Seminars in Oncology, 1996, vol. 23, (5 suppl. 10), pp. 3-15).*
Cisplatin Product Information, Bedford Labs Website, 2002, downloaded from Archival Storage Sep. 27, 2009.*
Abstract of Zaniboni et al (Journal of Chemotherapy, 2005, vol. 17, pp. 656-662).*
Abstract of Gatzemeier et al (2004 ASCO Annual Meeting Proceedings, abstract No. 7010).*
Weick, J.K., et al. (1991) J. Clin. Oncol. 9(7):1157-1162.
Johnson, D.H., et al. (1996) J. Clin. Oncol. 14(7):2054-2060.
Salomon, D.S., et al. (1995) Crit. Rev. Oncol. Hematol. 19:183-232.
Wells, A. (2000) Signal, 1:4-11 (ADIS International Ltd, Chester, UK).
Halatsch, M-E. et al. (2000) J. Neurosurg. 92:297-305.
Archer, G.E. et al. (1999) Clin. Cancer Res. 5:2646-2652.
de Bono, J.S. and Rowinsky, E.K. (2002) Trends in Mol. Medicine 8:S19-S26.
Dancey, J. and Sausville, E.A. (2003) Nature Rev. Drug Discovery 2:296-313.
Raben, D. et al. (2002) Semin. Oncol. 29:37-46.
Herbst, R.S. et al. (2001) Expert Opin. Biol. Ther. 1:719-732.
Magne, N. et al. (2003) Clin. Can. Res. 9:4735-4732.
Magne, N. et al. (2002) British Journal of Cancer 86:819-827.
Torrance, C.J. et al. (2000) Nature Med. 6:1024-1028.
Gupta, R.A. and DuBois, R.N. (2000) Nature Med. 6:974-975.
Tortora, et al. (2003) Clin. Cancer Res. 9:1566-1572.
Solomon, B. et al (2003) Int. J. Radiat. Oncol. Biol. Phys. 55:713-723.
Krishnan, S. et al. (2003) Frontiers in Bioscience 8, e1-13.
Huang, S. et al. (1999) Cancer Res. 59:1935-1940.
Contessa, J. N. et al. (1999) Clin. Cancer Res. 5:405-411.
Li, M. et al. (2002) Clin.Cancer Res. 8:3570-3578.
Ciardiello, F. et al. (2003) Clin. Cancer Res. 9:1546-1556.
Ciardiello, F. et al. (2000) Clin. Cancer Res. 6:3739-3747.
Grunwald, V. and Hidalgo, M. (2003) J. Nat. Cancer Inst. 95:851-867.
Seymour, L. (2003) Current Opin. Investig. Drugs 4(6):658-666.
Khalil, M.Y. et al. (2003) Expert Rev. Anticancer Ther.3:367-380.
Bulgaru, A.M. et al. (2003) Expert Rev. Anticancer Ther.3:269-279.
Kim, E.S. et al. (2001) Current Opinion Oncol. 13:506-513.
Arteaga, C.L. and Johnson, D.H. (2001) Current Opinion Oncol. 13:491-498.
Ciardiello, F. et al. (2000) Clin. Cancer Res. 6:2053-2063.

(Continued)

*Primary Examiner* — Karen A Canella

(57) ABSTRACT

The present invention provides a method for treating tumors or tumor metastases in a patient, comprising administering to the patient simultaneously or sequentially a therapeutically effective amount of an EGFR kinase inhibitor and cisplatin combination, with or without additional agents or treatments, such as other anti-cancer drugs or radiation therapy. The invention also encompasses a pharmaceutical composition that is comprised of an EGFR kinase inhibitor and cisplatin combination in combination with a pharmaceutically acceptable carrier. A preferred example of an EGFR kinase inhibitor that can be used in practicing this invention is the compound erlotinib HCl (also known as Tarceva™).

2 Claims, 8 Drawing Sheets

OTHER PUBLICATIONS

Ciardiello, F and Tortora, G. (2002) Expert Opin. Investig. Drugs 11:755-768.
Bunn, P.A. Jr, and Kelly K. (1998) Clin Cancer Res. 4(5):1087-1100.
Ten Bokkel, W.W., et al. (1999) Lung Cancer 26(2):85-94.
Giaccone, G, et al. (1998) J Clin. Oncol. 16:2133-2141.
Peters, G.J. et al. (1995) Semin. Oncol. 22(4 Suppl. 11):72-79.
Pollack, V.A., et al. (1999) J. Pharmacol. Exp. Ther. 291:739-48.
Bianco, C. et al. (2002) Clin. Cancer Res. 8(10):3250-3258.
Lee, M. et al. (1992) J Natl. Cancer Inst. Monogr. (13):117-123.
Kerbel, R. and Folkman, J. (2002) Nat. Rev. Cancer 2(10):727-39.
Ratain, et al. (2002) Proc. Am. Soc. Clin. Oncol.21 (Abstract 2115).
Phase III Tarceva trial in NSCLC completes enrollment Daily Drug News.com (Abstract); Prous Science [Sep. 18, 2002].
Krawczyk, Pawel et al. (2003) Annales Universitatis Mariae Curie-Sklodowska. Section D: Medicina 2003 58(1):113-117.
Higgins, Brian et al. (2004) Anti-Cancer Drugs 15(5):503-512.
Giaccone, G. et al. (2004) Journal of Clinical Oncology, Grune and Stratton (2004) 22(5):777-784.
Hammond, L A (2003) Clinical Lung Cancer 5 (No. suppl 1): S18-S20.
Sridhar, S. S. et al. (2003) Lancet Publishing Group, London, GB 4(7):397-406.
Gatzemeier et al. (2004) Proc. Am. Soc. Clin. Oncol. 23:617 (abstr 7010).
Burgos Fuster, L. M. et al. (2004) Clinical Lung Cancer 2004 United States 6 (No. suppl. 1) S24-S29.
Genentech Press Release Sep. 20, 2004, Tarceva Plus Gemcitabine Improves Survival Compared to Gemcitabine Alone in First-Line Pancreatic Cancer Patients.
Mininberg, R. S et al. (2003) Proc. Am. Soc. Clin. Oncol.22:2003 (abstr 2521).
Dragovich, T. et al. (2003) Proc. Am. Soc. Clin. Oncol.22:2003 (abstr 895).
Herbst, R. S. et al. (2004) Journal of Clinical Oncology 22:785-794.
Prados, M. et al. (2003) Proc. Am. Soc. Clin. Oncol.22: p. 99, 2003 (abstr 394).
Baselga, J. et al. (2000) Journal of Clinical Oncology 18:904-914.
Knecht, R. et al. (2003) Anticancer Research 23:2577-2583.
Hinerman, R. et al. (2004) Therapy 2004 United Kingdom 1:67-74.
Herbst, R.S. et al. (2004) Proc. Am. Soc. Clin. Oncol.23:2004 (abstr 7011).
Akita, R. W. et al. Seminars in Oncology, vol. 30, No. 3, suppl. 7 Jun. 2003: pp. 15-24.
International Preliminary Report on Patentability in PCT/EP2005/005737.
International Search Report in PCT/EP2005/005737.
Ng, S. S.W. et al. (2002) Molecular Cancer Technology, vol. 1, pp. 777-783.
Office Action (English translation) dated Jun. 29, 2009 from corresponding Russian application No. 2006146612.
Perez-Soler, et al. 2001 ASCO Annual Meeting, p. 1, Abstract 1235.

* cited by examiner

Figure 3. Single-dose pharmacokinetics of erlotinib 20 and 100mg/kg in non-tumour bearing female nu/nu athymic mice.

|  | 20 mg/kg | 100 mg/kg |
|---|---|---|
| Cmax (ng/ml) | 9100 | 24000 |
| Cmax/dose ([ng/ml]/[mg/kg]) | 455 | 240 |
| Tmax (h) | 0.5–1 | 0.5–1 |
| Tlast (h) | 8 | 24 |
| AUClast (h*ng/ml) | 33500 | 196000 |
| AUClast/dose ([h*ng/ml]/[mg/kg]) | 1680 | 1960 |
| CL/F (ml/min/kg) | 7.6 | 8.0 |
| $\lambda_z$ (1/hour) | 0.17 | 0.19 |
| $T_{1/2}$ (h) | 4.1 | 4.0 |
| MRT (h) | 5.6 | 8.2 |
| $V_z/F$ (l/kg) | 2.7 | 2.8 |

Cmax = peak plasma concentration; Tmax = time to peak plasma concentration; Tlast = time of last measurable concentration; AUC last = area under the plasma concentration-time curve from time zero to time of last measurable concentration; CL/F = apparent clearance; $\lambda_z$ = elimination rate constant; $T_{1/2}$ = plasma terminal half-life; MRT = mean residence time; $V_z/F$ = apparent volume of distribution.

Figure 5. Maximum tolerated dose assessment in non-tumour bearing athymic nude mice treated for 14 days (n=5).

| Compound | Dose (mg/kg) | Change in body weight at end of study (%) | Mortality |
|---|---|---|---|
| Vehicle control | 0 | 0 | 0 |
| Erlotinib in CMC/Tween | 400 | N/A | 5 |
| Erlotinib in CMC/Tween | 200 | N/A | 5 |
| Erlotinib in CMC/Tween | 100 | −1 | 0 |
| Erlotinib in CMC/Tween | 50 | −1 | 0 |
| Vehicle control | 0 | 2 | 0 |
| Cisplatin | 12 | N/A | 5 |
| Cisplatin | 9 | −15 | 2 |
| Cisplatin | 6 | 3 | 0 |
| Cisplatin | 3 | 4 | 0 |

N/A = not available; animals died before the end of the study.

COMBINED TREATMENT WITH CISPLATIN AND AN EPIDERMAL GROWTH FACTOR RECEPTOR KINASE INHIBITOR

CROSS-REFERENCE TO RELATED APPLICATIONS

This application claims the benefit of U.S. Provisional Application No. 60/576,790, filed Jun. 3, 2004, which is herein incorporated by reference in its entirety.

BACKGROUND OF THE INVENTION

The present invention is directed to compositions and methods for treating cancer patients. In particular, the present invention is directed to combined treatment of patients with cisplatin and an epidermal growth factor receptor (EGFR) kinase inhibitor.

Cancer is a generic name for a wide range of cellular malignancies characterized by unregulated growth, lack of differentiation, and the ability to invade local tissues and metastasize. These neoplastic malignancies affect, with various degrees of prevalence, every tissue and organ in the body.

A multitude of therapeutic agents have been developed over the past few decades for the treatment of various types of cancer. The most commonly used types of anticancer agents include: DNA-alkylating agents (e.g., cyclophosphamide, ifosfamide), antimetabolites (e.g., methotrexate, a folate antagonist, and 5-fluorouracil, a pyrimidine antagonist), microtubule disrupters (e.g., vincristine, vinblastine, paclitaxel), DNA intercalators (e.g., doxorubicin, daunomycin, cisplatin), and hormone therapy (e.g., tamoxifen, flutamide).

According to the National Cancer Institute, lung cancer is the single largest cause of cancer deaths in the United States and is responsible for nearly 30% of cancer deaths in the country. According to the World Health Organization, there are more than 1.2 million cases worldwide of lung and bronchial cancer each year, causing approximately 1.1 million deaths annually. NSCLC is the most common form of lung cancer and accounts for almost 80 percent of all cases. Treatment options for lung cancer are surgery, radiation therapy, and chemotherapy, either alone or in combination, depending on the form and stage of the cancer. For advanced NSCLC, agents that have been shown to be active include cisplatin (CisP; e.g. Platinol®), carboplatin, paclitaxel, docetaxel, topotecan, irinotecan, vinorelbine, gemcitabine, and the EGFR kinase inhibitors gefitinib and erlotinib. Cisplatin-containing and carboplatin-containing combination chemotherapy regimens have been shown to produce objective response rates that are higher than those achieved with single-agent chemotherapy (Weick, J. K., et al. (1991) J. Clin. Oncol. 9(7):1157-1162). It has been reported that paclitaxel has single-agent activity in stage IV patients, with response rates in the range of 21% to 24% (Murphy W. K., et al. (1993) J. Natl. Cancer Inst. 85(5):384-388). Paclitaxel combinations have shown relatively high response rates, significant 1 year survival, and palliation of lung cancer symptoms (Johnson D. H., et al. (1996) J. Clin. Oncol. 14(7):2054-2060). With a paclitaxel plus carboplatin regimen, response rates have been in the range of 27% to 53% with 1-year survival rates of 32% to 54%. However, efficacy of such treatments is such that no specific regimen can be regarded as standard therapy at present.

Over-expression of the epidermal growth factor receptor (EGFR) kinase, or its ligand TGF-alpha, is frequently associated with many cancers, including breast, lung, colorectal and head and neck cancers (Salomon D. S., et al. (1995) Crit. Rev. Oncol. Hematol. 19:183-232; Wells, A. (2000) Signal, 1:4-11), and is believed to contribute to the malignant growth of these tumors. A specific deletion-mutation in the EGFR gene has also been found to increase cellular tumorigenicity (Halatsch, M-E. et al. (2000) J. Neurosurg. 92:297-305; Archer, G. E. et al. (1999) Clin. Cancer Res. 5:2646-2652). Activation of EGFR stimulated signaling pathways promote multiple processes that are potentially cancer-promoting, e.g. proliferation, angiogenesis, cell motility and invasion, decreased apoptosis and induction of drug resistance. The development for use as anti-tumor agents of compounds that directly inhibit the kinase activity of the EGFR, as well as antibodies that reduce EGFR kinase activity by blocking EGFR activation, are areas of intense research effort (de Bono J. S. and Rowinsky, E. K. (2002) Trends in Mol. Medicine 8:S19-S26; Dancey, J. and Sausville, E. A. (2003) Nature Rev. Drug Discovery 2:92-313). Several studies have demonstrated or disclosed that some EGFR kinase inhibitors can improve tumor cell or neoplasia killing when used in combination with certain other anti-cancer or chemotherapeutic agents or treatments (e.g. Raben, D. et al. (2002) Semin. Oncol. 29:37-46; Herbst, R. S. et al. (2001) Expert Opin. Biol. Ther. 1:719-732; Magne, N et al. (2003) Clin. Can. Res. 9:4735-4732; Magne, N. et al. (2002) British Journal of Cancer 86:819-827; Torrance, C. J. et al. (2000) Nature Med. 6:1024-1028; Gupta, R. A. and DuBois, R. N. (2000) Nature Med. 6:974-975; Tortora, et al. (2003) Clin. Cancer Res. 9:1566-1572; Solomon, B. et al (2003) Int. J. Radiat. Oncol. Biol. Phys. 55:713-723; Krishnan, S. et al. (2003) Frontiers in Bioscience 8, e1-13; Huang, S et al. (1999) Cancer Res. 59:1935-1940; Contessa, J. N. et al. (1999) Clin. Cancer Res. 5:405-411; Li, M. et al. Clin. (2002) Cancer Res. 8:3570-3578; Ciardiello, F. et al. (2003) Clin. Cancer Res. 9:1546-1556; Ciardiello, F. et al. (2000) Clin. Cancer Res. 6:3739-3747; Grunwald, V. and Hidalgo, M. (2003) J. Nat. Cancer Inst. 95:851-867; Seymour L. (2003) Current Opin. Investig. Drugs 4(6):658-666; Khalil, M. Y. et al. (2003) Expert Rev. Anticancer Ther. 3:367-380; Bulgaru, A. M. et al. (2003) Expert Rev. Anticancer Ther. 3:269-279; Dancey, J. and Sausville, E. A. (2003) Nature Rev. Drug Discovery 2:92-313; Kim, E. S. et al. (2001) Current Opinion Oncol. 13:506-513; Arteaga, C. L. and Johnson, D. H. (2001) Current Opinion Oncol. 13:491-498; Ciardiello, F. et al. (2000) Clin. Cancer Res. 6:2053-2063; Patent Publication Nos: U.S. 2003/0108545; U.S. 2002/0076408; and U.S. 2003/0157104; and International Patent Publication Nos: WO 99/60023; WO 01/12227; WO 02/055106; WO 03/088971; WO 01/34574; WO 01/76586; WO 02/05791; and WO 02/089842).

An anti-neoplastic drug would ideally kill cancer cells selectively, with a wide therapeutic index relative to its toxicity towards non-malignant cells. It would also retain its efficacy against malignant cells, even after prolonged exposure to the drug. Unfortunately, none of the current chemotherapies possess such an ideal profile. Instead, most possess very narrow therapeutic indexes. Furthermore, cancerous cells exposed to slightly sub-lethal concentrations of a chemotherapeutic agent will very often develop resistance to such an agent, and quite often cross-resistance to several other antineoplastic agents as well.

Thus, there is a need for more efficacious treatment for neoplasia and other proliferative disorders. Strategies for enhancing the therapeutic efficacy of existing drugs have involved changes in the schedule for their administration, and also their use in combination with other anticancer or biochemical modulating agents. Combination therapy is well known as a method that can result in greater efficacy and diminished side effects relative to the use of the therapeutically relevant dose of each agent alone. In some cases, the efficacy of the drug combination is additive (the efficacy of the combination is approximately equal to the sum of the effects of each drug alone), but in other cases the effect is synergistic (the efficacy of the combination is greater than the sum of the effects of each drug given alone).

However, there remains a critical need for improved treatments for lung and other cancers. This invention provides anti-cancer combination therapies that reduce the dosages for individual components required for efficacy, thereby decreasing side effects associated with each agent, while maintaining or increasing therapeutic value. The invention described herein provides new drug combinations, and methods for using drug combinations in the treatment of lung and other cancers.

SUMMARY OF THE INVENTION

The present invention provides a method for treating tumors or tumor metastases in a patient, comprising administering to the patient simultaneously or sequentially a therapeutically effective amount of an EGFR kinase inhibitor and cisplatin combination, with or without additional agents or treatments, such as other anti-cancer drugs or radiation therapy.

The invention also encompasses a pharmaceutical composition that is comprised of an EGFR kinase inhibitor and cisplatin combination in combination with a pharmaceutically acceptable carrier.

A preferred example of an EGFR kinase inhibitor that can be used in practicing this invention is the compound erlotinib HCl (also known as Tarceva™).

BRIEF DESCRIPTION OF THE FIGURES

FIG. 3: Single-dose pharmacokinetics of erlotinib 20 and 100 mg/kg in non-tumour bearing female nu/nu athymic mice.

FIG. 5: Maximum tolerated dose assessment in non-tumour bearing athymic nude mice treated for 14 days (n=5).

DETAILED DESCRIPTION OF THE INVENTION

Figure 1:
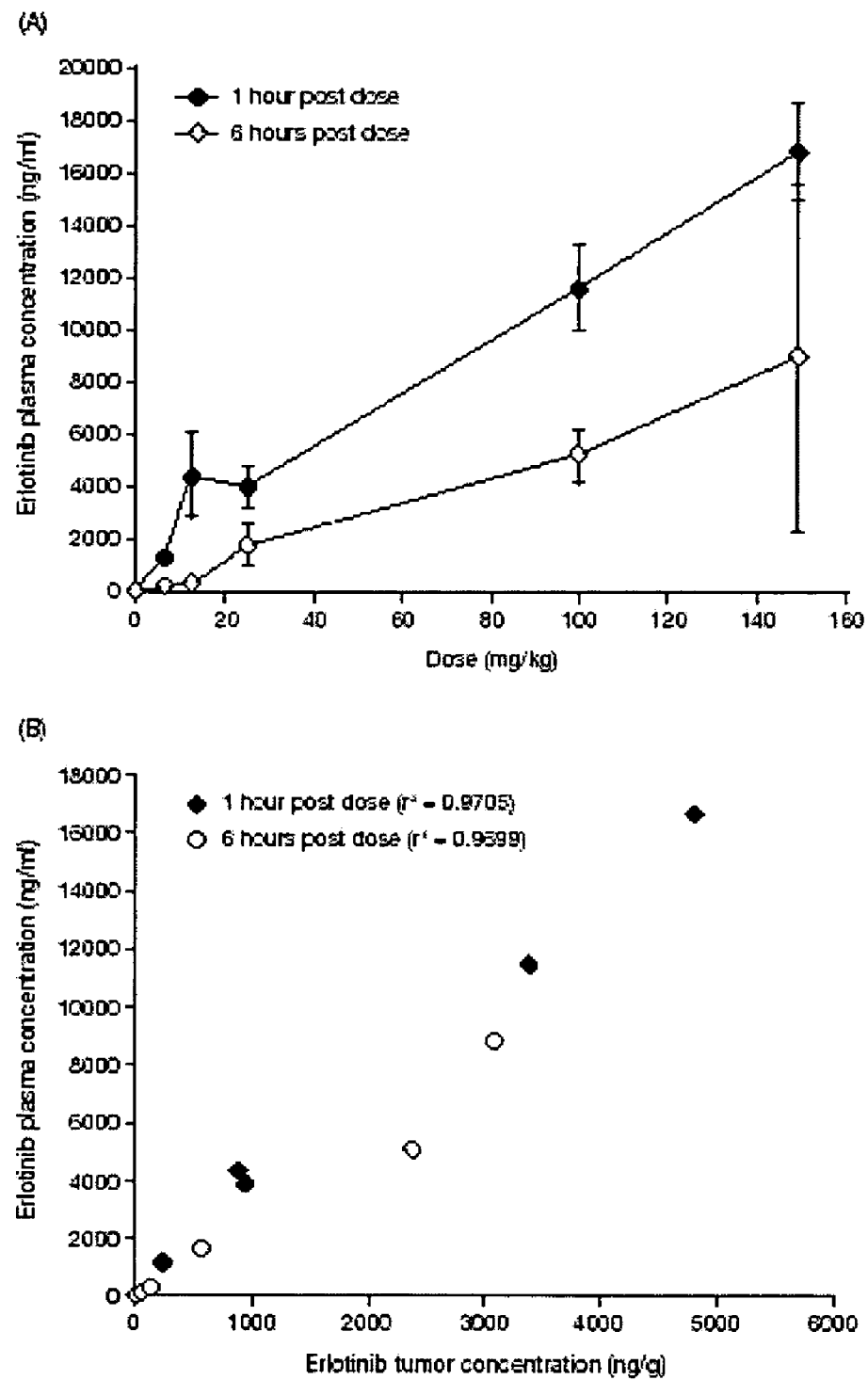
FIG. 1: Erlotinib plasma concentrations over time (A) Dose-dependent plasma concentrations (B) Correlation between tumor drug concentrations and plasma drug concentrations. Tumor-bearing mice were given daily oral doses of erlotinib at 0, 6.3, 12.5, 25.0, 100.0 or 150.0 mg/kg for 21 days. On day 28 post tumor implant, blood (from the retro-orbital sinus) and tumor samples were collected at 1 and 6 hours post dosing. Concentrations of erlotinib were determined using LC-MS/MS. Values are means±SD, n=3.

The term "cancer" in an animal refers to the presence of cells possessing characteristics typical of cancer-causing cells, such as uncontrolled proliferation, immortality, metastatic potential, rapid growth and proliferation rate, and certain characteristic morphological features. Often, cancer cells will be in the form of a tumor, but such cells may exist alone within an animal, or may circulate in the blood stream as independent cells, such as leukemic cells.

"Abnormal cell growth", as used herein, unless otherwise indicated, refers to cell growth that is independent of normal regulatory mechanisms (e.g., loss of contact inhibition). This includes the abnormal growth of: (1) tumor cells (tumors) that proliferate by expressing a mutated tyrosine kinase or over-expression of a receptor tyrosine kinase; (2) benign and malignant cells of other proliferative diseases in which aberrant tyrosine kinase activation occurs; (4) any tumors that proliferate by receptor tyrosine kinases; (5) any tumors that proliferate by aberrant serine/threonine kinase activation; and (6) benign and malignant cells of other proliferative diseases in which aberrant serine/threonine kinase activation occurs.

The term "treating" as used herein, unless otherwise indicated, means reversing, alleviating, inhibiting the progress of, or preventing, either partially or completely, the growth of tumors, tumor metastases, or other cancer-causing or neoplastic cells in a patient. The term "treatment" as used herein, unless otherwise indicated, refers to the act of treating.

The phrase "a method of treating" or its equivalent, when applied to, for example, cancer refers to a procedure or course of action that is designed to reduce or eliminate the number of cancer cells in an animal, or to alleviate the symptoms of a cancer. "A method of treating" cancer or another proliferative disorder does not necessarily mean that the cancer cells or other disorder will, in fact, be eliminated, that the number of cells or disorder will, in fact, be reduced, or that the symptoms of a cancer or other disorder will, in fact, be alleviated. Often, a method of treating cancer will be performed even with a low likelihood of success, but which, given the medical history and estimated survival expectancy of an animal, is nevertheless deemed an overall beneficial course of action.

The term "therapeutically effective agent" means a composition that will elicit the biological or medical response of a tissue, system, animal or human that is being sought by the researcher, veterinarian, medical doctor or other clinician.

The term "therapeutically effective amount" or "effective amount" means the amount of the subject compound or combination that will elicit the biological or medical response of a tissue, system, animal or human that is being sought by the researcher, veterinarian, medical doctor or other clinician.

The data presented in the Examples herein below demonstrate that co-administration of cisplatin with an EGFR kinase inhibitor is effective for treatment of patients with advanced cancers, such as lung cancer. Accordingly, the present invention provides a method for treating tumors or tumor metastases in a patient, comprising administering to the patient simultaneously or sequentially a therapeutically effective amount of an EGFR kinase inhibitor and cisplatin combination. In one embodiment the tumors or tumor metastases to be treated are lung tumors or tumor metastases.

The present invention further provides a method for treating tumors or tumor metastases in a patient, comprising administering to the patient simultaneously or sequentially a therapeutically effective amount of an EGFR kinase inhibitor and cisplatin combination, and in addition, one or more other cytotoxic, chemotherapeutic or anti-cancer agents, or compounds that enhance the effects of such agents.

In the context of this invention, additional other cytotoxic, chemotherapeutic or anti-cancer agents, or compounds that enhance the effects of such agents, include, for example: alkylating agents or agents with an alkylating action, such as cyclophosphamide (CTX; e.g. Cytoxan®), chlorambucil (CHL; e.g. Leukeran®), busulfan (e.g. Myleran®), melphalan, carmustine (BCNU), streptozotocin, triethylenemelamine (TEM), mitomycin C, and the like; anti-metabolites, such as methotrexate (MTX), etoposide (VP16; e.g. Vepesid®), 6-mercaptopurine (6MP), 6-thioguanine (6TG), cytarabine (Ara-C), 5-fluorouracil (5-FU), capecitabine (e.g. Xeloda®), dacarbazine (DTIC), and the like; antibiotics, such as actinomycin D, doxorubicin (DXR; e.g. Adriamycin®), daunorubicin (daunomycin), bleomycin, mithramycin and the like; alkaloids, such as vinca alkaloids such as vincristine (VCR), vinblastine, and the like; and other antitumor agents, such as paclitaxel (e.g. Taxol®) and pactitaxel derivatives, the cytostatic agents, glucocorticoids such as dexamethasone (DEX; e.g. Decadron®) and corticosteroids such as prednisone, nucleoside enzyme inhibitors such as hydroxyurea, amino acid depleting enzymes such as asparaginase, leucovorin, folinic acid and other folic acid derivatives, and similar, diverse antitumor agents. The following agents may also be used as additional agents: arnifostine (e.g. Ethyol®), dactinomycin, mechlorethamine (nitrogen mustard), streptozocin, cyclophosphamide, lomustine (CCNU), doxorubicin lipo (e.g. Doxil®), gemcitabine (e.g. Gemzar®), daunorubicin lipo (e.g. Daunoxome®), procarbazine, mitomycin, docetaxel (e.g. Taxotere®), aldesleukin, carboplatin, cladribine, camptothecin, CPT 11 (irinotecan), 10-hydroxy 7-ethyl-camptothecin (SN38), floxuridine, fludarabine, ifosfamide, idarubicin, mesna, interferon alpha, interferon beta, mitoxantrone, topotecan, leuprolide, megestrol, melphalan, mercaptopurine, plicamycin, mitotane, pegaspargase, pentostatin, pipobroman, plicamycin, tamoxifen, teniposide, testolactone, thioguanine, thiotepa, uracil mustard, vinorelbine, chlorambucil.

The present invention further provides a method for treating tumors or tumor metastases in a patient, comprising administering to said patient simultaneously or sequentially a therapeutically effective amount of an EGFR kinase inhibitor and cisplatin combination, and in addition, one or more anti-hormonal agents. As used herein, the term "anti-hormonal agent" includes natural or synthetic organic or peptidic compounds that act to regulate or inhibit hormone action on tumors.

Antihormonal agents include, for example: steroid receptor antagonists, anti-estrogens such as tamoxifen, raloxifene, aromatase inhibiting 4(5)-imidazoles, other aromatase inhibitors, 42-hydroxytamoxifen, trioxifene, keoxifene, LY 117018, onapristone, and toremifene (e.g. Fareston®); antiandrogens such as flutamide, nilutamide, bicalutamide, leuprolide, and goserelin; and pharmaceutically acceptable salts, acids or derivatives of any of the above; agonists and/or antagonists of glycoprotein hormones such as follicle stimulating hormone (FSH), thyroid stimulating hormone (TSH), and luteinizing hormone (LH) and LHRH (leuteinizing hormone-releasing hormone); the LHRH agonist goserelin acetate, commercially available as Zoladex® (AstraZeneca); the LHRH antagonist D-alaninamide N-acetyl-3-(2-naphthalenyl)-D-alanyl-4-chloro-D-phenylalanyl-3-(3-pyridinyl)-D-alanyl-L-seryl-N-6-(3-pyridinylcarbonyl)-L-lysyl-N-6-(3-pyridinylcarbonyl)-D-lysyl-L-leucyl-N6-(1-methylethyl)-L-lysyl-L-proline (e.g Antide®, Ares-Serono); the LHRH antagonist ganirelix acetate; the steroidal anti-androgens cyproterone acetate (CPA) and megestrol acetate, commercially available as Megace® (Bristol-Myers Oncology); the nonsteroidal anti-androgen flutamide (2-methyl-N-[4,20-nitro-3-(trifluoromethyl) phenylpropanamide), commercially available as Eulexin® (Schering Corp.); the nonsteroidal anti-androgen nilutamide, (5,5-dimethyl-3-[4-nitro-3-(trifluoromethyl-4'-nitrophenyl)-4,4-dimethyl-imidazolidine-dione); and antagonists for other non-permissive receptors, such as antagonists for RAR, RXR, TR, VDR, and the like.

The use of the cytotoxic and other anticancer agents described above in chemotherapeutic regimens is generally well characterized in the cancer therapy arts, and their use herein falls under the same considerations for monitoring tolerance and effectiveness and for controlling administration routes and dosages, with some adjustments. For example, the actual dosages of the cytotoxic agents may vary depending upon the patient's cultured cell response determined by using histoculture methods. Generally, the dosage will be reduced compared to the amount used in the absence of additional other agents.

Typical dosages of an effective cytotoxic agent can be in the ranges recommended by the manufacturer, and where indicated by in vitro responses or responses in animal models, can be reduced by up to about one order of magnitude concentration or amount. Thus, the actual dosage will depend upon the judgment of the physician, the condition of the patient, and the effectiveness of the therapeutic method based on the in vitro responsiveness of the primary cultured malignant cells or histocultured tissue sample, or the responses observed in the appropriate animal models.

In the context of this invention, of the above additional other cytotoxic, chemotherapeutic or anticancer agents the compounds gemcitabine, taxotere, and vinorelbine are preferred.

The present invention further provides a method for treating tumors or tumor metastases in a patient, comprising administering to said patient simultaneously or sequentially a therapeutically effective amount of an EGFR kinase inhibitor and cisplatin combination, and in addition one or more angiogenesis inhibitors.

Anti-angiogenic agents include, for example: VEGFR inhibitors, such as SU-5416 and SU-6668 (Sugen Inc. of South San Francisco, Calif., USA), or as described in, for example International Application Nos. WO 99/24440, WO 99/62890, WO 95/21613, WO 99/61422, WO 98/50356, WO 99/10349, WO 97/32856, WO 97/22596, WO 98/54093, WO 98/02438, WO 99/16755, and WO 98/02437, and U.S. Pat. Nos. 5,883,113, 5,886,020, 5,792,783, 5,834,504 and 6,235,764; VEGF inhibitors such as IM862 (Cytran Inc. of Kirkland, Wash., USA); angiozyme, a synthetic ribozyme from Ribozyme (Boulder, Colo.) and Chiron (Emeryville, Calif.); and antibodies to VEGF, such as bevacizumab (e.g. Avastin™, Genentech, South San Francisco, Calif.), a recombinant humanized antibody to VEGF; integrin receptor antagonists and integrin antagonists, such as to $\alpha_v\beta_3$, $\alpha_v\beta_5$ and $\alpha_v\beta_6$ integrins, and subtypes thereof, e.g. cilengitide (EMD 121974), or the anti-integrin antibodies, such as for example $\alpha_v\beta_3$ specific humanized antibodies (e.g. Vitaxin®); factors such as IFN-alpha (U.S. Pat. Nos. 41,530,901, 4,503,035, and 5,231,176); angiostatin and plasminogen fragments (e.g. kringle 1-4, kringle 5, kringle 1-3 (O'Reilly, M. S. et al. (1994) Cell 79:315-328; Cao et al. (1996) J. Biol. Chem. 271: 29461-29467; Cao et al. (1997) J. Biol. Chem. 272:22924-22928); endostatin (O'Reilly, M. S. et al. (1997) Cell 88:277; and International Patent Publication No. WO 97/15666); thrombospondin (TSP-1; Frazier, (1991) Curr. Opin. Cell Biol. 3:792); platelet factor 4 (PF4); plasminogen activator/urokinase inhibitors; urokinase receptor antagonists; heparinases; fumagillin analogs such as TNP-4701; suramin and suramin analogs; angiostatic steroids; bFGF antagonists; flk-1 and flt-1 antagonists; anti-angiogenesis agents such as MMP-2 (matrix-metalloproteinase 2) inhibitors and MMP-9 (matrix-metalloproteinase 9) inhibitors. Examples of useful matrix metalloproteinase inhibitors are described in International Patent Publication Nos. WO 96/33172, WO 96/27583, WO 98/07697, WO 98/03516, WO 98/34918, WO 98/34915, WO 98/33768, WO 98/30566, WO 90/05719, WO 99/52910, WO 99/52889, WO 99/29667, and WO 99/07675, European Patent Publication Nos. 818,442, 780,386, 1,004,578, 606,046, and 931,788; Great Britain Patent Publication No. 9912961, and U.S. Pat. Nos. 5,863,949 and 5,861,510. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

The present invention further provides a method for treating tumors or tumor metastases in a patient, comprising administering to the patient simultaneously or sequentially a therapeutically effective amount of an EGFR kinase inhibitor and cisplatin combination, and in addition one or more tumor cell pro-apoptotic or apoptosis-stimulating agents.

The present invention further provides a method for treating tumors or tumor metastases in a patient, comprising administering to said patient simultaneously or sequentially a therapeutically effective amount of an EGFR kinase inhibitor and cisplatin combination, and in addition one or more signal transduction inhibitors.

Signal transduction inhibitors include, for example: erbB2 receptor inhibitors, such as organic molecules, or antibodies that bind to the erbB2 receptor, for example, trastuzumab (e.g. Herceptin®); inhibitors of other protein tyrosine-kinases, e.g. imitinib (e.g. Gleevec®); ras inhibitors; raf inhibitors; MEK inhibitors; mTOR inhibitors; cyclin dependent kinase inhibitors; protein kinase C inhibitors; and PDK-1 inhibitors (see Dancey, J. and Sausville, E. A. (2003) Nature Rev. Drug Discovery 2:92-313, for a description of several examples of such inhibitors, and their use in clinical trials for the treatment of cancer).

ErbB2 receptor inhibitors include, for example: ErbB2 receptor inhibitors, such as GW-282974 (Glaxo Wellcome plc), monoclonal antibodies such as AR-209 (Aronex Pharmaceuticals Inc. of The Woodlands, Tex., USA) and 2B-1 (Chiron), and erbB2 inhibitors such as those described in International Publication Nos. WO 98/02434, WO 99/35146, WO 99/35132, WO 98/02437, WO 97/13760, and WO 95/19970, and U.S. Pat. Nos. 5,587,458, 5,877,305, 6,465,449 and 6,541,481.

The present invention further thus provides a method for treating tumors or tumor metastases in a patient, comprising administering to said patient simultaneously or sequentially a therapeutically effective amount of an EGFR kinase inhibitor and cisplatin combination, and in addition an anti-HER2 antibody or an immunotherapeutically active fragment thereof.

The present invention further provides a method for treating tumors or tumor metastases in a patient, comprising administering to said patient simultaneously or sequentially a therapeutically effective amount of an EGFR kinase inhibitor and cisplatin combination, and in addition one or more additional anti-proliferative agents.

Additional antiproliferative agents include, for example: Inhibitors of the enzyme farnesyl protein transferase and inhibitors of the receptor tyrosine kinase PDGFR, including the compounds disclosed and claimed in U.S. Pat. Nos. 6,080,769, 6,194,438, 6,258,824, 6,586,447, 6,071,935, 6,495,564, 6,150,377, 6,596,735 and 6,479,513, and International Patent Publication WO 01/40217.

The present invention further provides a method for treating tumors or tumor metastases in a patient, comprising administering to the patient simultaneously or sequentially a therapeutically effective amount of an EGFR kinase inhibitor and cisplatin combination, and in addition a COX II (cyclooxygenase II) inhibitor. Examples of useful COX-11 inhibitors include alecoxib (e.g. Celebrex™), valdecoxib, and rofecoxib.

The present invention further provides a method for treating tumors or tumor metastases in a patient, comprising administering to the patient simultaneously or sequentially a therapeutically effective amount of an EGFR kinase inhibitor and cisplatin combination, and in addition treatment with radiation or a radiopharmaceutical.

The source of radiation can be either external or internal to the patient being treated. When the source is external to the patient, the therapy is known as external beam radiation therapy (EBRT). When the source of radiation is internal to the patient, the treatment is called brachytherapy (BT). Radioactive atoms for use in the context of this invention can be selected from the group including, but not limited to, radium, cesium-137, iridium-192, americium-241, gold-198, cobalt-57, copper-67, technetium-99, iodine-123, iodine-131, and indium-111. Where the EGFR kinase inhibitor according to this invention is an antibody, it is also possible to label the antibody with such radioactive isotopes.

Radiation therapy is a standard treatment for controlling unresectable or inoperable tumors and/or tumor metastases. Improved results have been seen when radiation therapy has been combined with chemotherapy. Radiation therapy is based on the principle that high-dose radiation delivered to a target area will result in the death of reproductive cells in both tumor and normal tissues. The radiation dosage regimen is generally defined in terms of radiation absorbed dose (Gy), time and fractionation, and must be carefully defined by the oncologist. The amount of radiation a patient receives will depend on various considerations, but the two most important are the location of the tumor in relation to other critical structures or organs of the body, and the extent to which the tumor has spread. A typical course of treatment for a patient undergoing radiation therapy will be a treatment schedule over a 1 to 6 week period, with a total dose of between 10 and 80 Gy administered to the patient in a single daily fraction of about 1.8 to 2.0 Gy, 5 days a week. In a preferred embodiment of this invention there is synergy when tumors in human patients are treated with the combination treatment of the invention and radiation. In other words, the inhibition of tumor growth by means of the agents comprising the combination of the invention is enhanced when combined with radiation, optionally with additional chemotherapeutic or anticancer agents. Parameters of adjuvant radiation therapies are, for example, contained in International Patent Publication WO 99/60023.

The present invention further provides a method for treating tumors or tumor metastases in a patient, comprising administering to the patient simultaneously or sequentially a therapeutically effective amount of an EGFR kinase inhibitor and cisplatin combination, and in addition treatment with one or more agents capable of enhancing antitumor immune responses.

Agents capable of enhancing antitumor immune responses include, for example: CTLA4 (cytotoxic lymphocyte antigen 4) antibodies (e.g. MDX-CTLA4), and other agents capable of blocking CTLA4. Specific CTLA4 antibodies that can be used in the present invention include those described in U.S. Pat. No. 6,682,736.

The present invention further provides a method for reducing the side effects caused by the treatment of tumors or tumor metastases in a patient with an EGFR kinase inhibitor or cisplatin, comprising administering to the patient simultaneously or sequentially a therapeutically effective amount of an EGFR kinase inhibitor and cisplatin combination, in amounts that are effective to produce an additive, or a super-additive or synergistic antitumor effect, and that are effective at inhibiting the growth of the tumor.

The present invention further provides a method for the treatment of cancer, comprising administering to a subject in need of such treatment (i) an effective first amount of an EGFR kinase inhibitor, or a pharmaceutically acceptable salt thereof; and (ii) an effective second amount of cisplatin.

The present invention also provides a method for the treatment of cancer, comprising administering to a subject in need of such treatment (i) a sub-therapeutic first amount of the EGFR kinase inhibitor erlotinib, or a pharmaceutically acceptable salt thereof, and (ii) a sub-therapeutic second amount of cisplatin.

Additionally, the present invention provides a pharmaceutical composition comprising an EGFR inhibitor and cisplatin in a pharmaceutically acceptable carrier.

As used herein, the term "patient" preferably refers to a human in need of treatment with an EGFR kinase inhibitor for any purpose, and more preferably a human in need of such a treatment to treat cancer, or a precancerous condition or lesion. However, the term "patient" can also refer to non-human animals, preferably mammals such as dogs, cats, horses, cows, pigs, sheep and non-human primates, among others, that are in need of treatment with an EGFR kinase inhibitor.

In a preferred embodiment, the patient is a human in need of treatment for cancer, or a precancerous condition or lesion. The cancer is preferably any cancer treatable, either partially or completely, by administration of an EGFR kinase inhibitor. The cancer may be, for example, lung cancer, non small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, chronic or acute leukemia, lymphocytic lymphomas, neoplasms of the central nervous system (CNS), spinal axis tumors, brain stem glioma, glioblastoma multiforme, astrocytomas, schwannomas, ependymomas, medulloblastomas, meningiomas, squamous cell carcinomas, pituitary adenomas, including refractory versions of any of the above cancers, or a combination of one or more of the above cancers. The precancerous condition or lesion includes, for example, the group consisting of oral leukoplakia, actinic keratosis (solar keratosis), precancerous polyps of the colon or rectum, gastric epithelial dysplasia, adenomatous dysplasia, hereditary nonpolyposis colon cancer syndrome (HNPCC), Barrett's esophagus, bladder dysplasia, and precancerous cervical conditions.

For purposes of the present invention, "co-administration of" and "co-administering" cisplatin with an EGFR kinase inhibitor (both components referred to hereinafter as the "two active agents") refer to any administration of the two active agents, either separately or together, where the two active agents are administered as part of an appropriate dose regimen designed to obtain the benefit of the combination therapy. Thus, the two active agents can be administered either as part of the same pharmaceutical composition or in separate pharmaceutical compositions. Cisplatin can be administered prior to, at the same time as, or subsequent to administration of the EGFR kinase inhibitor, or in some combination thereof. Where the EGFR kinase inhibitor is administered to the patient at repeated intervals, e.g., during a standard course of treatment, cisplatin can be administered prior to, at the same time as, or subsequent to, each administration of the EGFR kinase inhibitor, or some combination thereof, or at different intervals in relation to the EGFR kinase inhibitor treatment, or in a single dose prior to, at any time during, or subsequent to the course of treatment with the EGFR kinase inhibitor.

The EGFR kinase inhibitor will typically be administered to the patient in a dose regimen that provides for the most effective treatment of the cancer (from both efficacy and safety perspectives) for which the patient is being treated, as known in the art, and as disclosed, e.g. in International Patent Publication No. WO 01/34574. In conducting the treatment method of the present invention, the EGFR kinase inhibitor can be administered in any effective manner known in the art, such as by oral, topical, intravenous, intra-peritoneal, intramuscular, intra-articular, subcutaneous, intranasal, intra-ocular, vaginal, rectal, or intradermal routes, depending upon the type of cancer being treated, the type of EGFR kinase inhibitor being used (e.g., small molecule, antibody, RNAi or antisense construct), and the medical judgement of the prescribing physician as based, e.g., on the results of published clinical studies.

The amount of EGFR kinase inhibitor administered and the timing of EGFR kinase inhibitor administration will depend on the type (species, gender, age, weight, etc.) and condition of the patient being treated, the severity of the disease or condition being treated, and on the route of administration. For example, small molecule EGFR kinase inhibitors can be administered to a patient in doses ranging from 0.001 to 100 mg/kg of body weight per day or per week in single or divided doses, or by continuous infusion (see for example, International Patent Publication No. WO 01/34574). In particular, erlotinib HCl can be administered to a patient in doses ranging from 5-200 mg per day, or 100-1600 mg per week, in single or divided doses, or by continuous infusion. A preferred dose is 150 mg/day. Antibody-based EGFR kinase inhibitors, or antisense, RNAi or ribozyme constructs, can be administered to a patient in doses ranging from 0.1 to 100 mg/kg of body weight per day or per week in single or divided doses, or by continuous infusion. In some instances, dosage levels below the lower limit of the aforesaid range may be more than adequate, while in other cases still larger doses may be employed without causing any harmful side effect, provided that such larger doses are first divided into several small doses for administration throughout the day.

The EGFR kinase inhibitors and cisplatin can be administered either separately or together by the same or different routes, and in a wide variety of different dosage forms. For example, the EGFR kinase inhibitor is preferably administered orally or parenterally, whereas cisplatin is preferably administered parenterally. Where the EGFR kinase inhibitor is erlotinib HCl (Tarceva™), oral administration is preferable.

The EGFR kinase inhibitor can be administered with various pharmaceutically acceptable inert carriers in the form of tablets, capsules, lozenges, troches, hard candies, powders, sprays, creams, salves, suppositories, jellies, gels, pastes, lotions, ointments, elixirs, syrups, and the like. Administration of such dosage forms can be carried out in single or multiple doses. Carriers include solid diluents or fillers, sterile aqueous media and various non-toxic organic solvents, etc. Oral pharmaceutical compositions can be suitably sweetened and/or flavored.

The EGFR kinase inhibitor and cisplatin can be combined together with various pharmaceutically acceptable inert carriers in the form of sprays, creams, salves, suppositories, jellies, gels, pastes, lotions, ointments, and the like. Administration of such dosage forms can be carried out in single or multiple doses. Carriers include solid diluents or fillers, sterile aqueous media, and various non-toxic organic solvents, etc.

All formulations comprising proteinaceous EGFR kinase inhibitors should be selected so as to avoid denaturation and/or degradation and loss of biological activity of the inhibitor.

Methods of preparing pharmaceutical compositions comprising an EGFR kinase inhibitor are known in the art, and are described, e.g. in International Patent Publication No. WO 01/34574. Methods of preparing pharmaceutical compositions comprising cisplatin are also well known in the art. In view of the teaching of the present invention, methods of preparing pharmaceutical compositions comprising both an EGFR kinase inhibitor and cisplatin will be apparent from the above-cited publications and from other known references, such as Remington's Pharmaceutical Sciences, Mack Publishing Company, Easton, Pa., 18$^{th}$ edition (1990).

For oral administration of EGFR kinase inhibitors, tablets containing one or both of the active agents are combined with any of various excipients such as, for example, micro-crystalline cellulose, sodium citrate, calcium carbonate, dicalcium phosphate and glycine, along with various disintegrants such as starch (and preferably corn, potato or tapioca starch), alginic acid and certain complex silicates, together with granulation binders like polyvinyl pyrrolidone, sucrose, gelatin and acacia. Additionally, lubricating agents such as magnesium stearate, sodium lauryl sulfate and talc are often very useful for tableting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the EGFR kinase inhibitor may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration of either or both of the active agents, solutions in either sesame or peanut oil or in aqueous propylene glycol may be employed, as well as sterile aqueous solutions comprising the active agent or a corresponding water-soluble salt thereof. Such sterile aqueous solutions are preferably suitably buffered, and are also preferably rendered isotonic, e.g., with sufficient saline or glucose. These particular aqueous solutions are especially suitable for intravenous, intramuscular, subcutaneous and intraperitoneal injection purposes. The oily solutions are suitable for intra-articular, intramuscular and subcutaneous injection purposes. The preparation of all these solutions under sterile conditions is readily accomplished by standard pharmaceutical techniques well known to those skilled in the art. Any parenteral formulation selected for administration of proteinaceous EGFR kinase inhibitors should be selected so as to avoid denaturation and loss of biological activity of the inhibitor.

Additionally, it is possible to topically administer either or both of the active agents, by way of, for example, creams, lotions, jellies, gels, pastes, ointments, salves and the like, in accordance with standard pharmaceutical practice. For example, a topical formulation comprising either an EGFR kinase inhibitor or cisplatin in about 0.1% (w/v) to about 5% (w/v) concentration can be prepared.

For veterinary purposes, the active agents can be administered separately or together to animals using any of the forms and by any of the routes described above. In a preferred embodiment, the EGFR kinase inhibitor is administered in the form of a capsule, bolus, tablet, liquid drench, by injection or as an implant. As an alternative, the EGFR kinase inhibitor can be administered with the animal feedstuff, and for this purpose a concentrated feed additive or premix may be prepared for a normal animal feed. The cisplatin is preferably administered in the form of liquid drench, by injection or as an implant. Such formulations are prepared in a conventional manner in accordance with standard veterinary practice.

The present invention further provides a kit comprising a single container comprising both an EGFR kinase inhibitor and cisplatin. The present invention further provides a kit comprising a first container comprising an EGFR kinase inhibitor and a second container comprising cisplatin. In a preferred embodiment, the kit containers may further include a pharmaceutically acceptable carrier. The kit may further include a sterile diluent, which is preferably stored in a separate additional container. The kit may further include a package insert comprising printed instructions directing the use of the combined treatment as a method for treating cancer.

As used herein, the term "EGFR kinase inhibitor" refers to any EGFR kinase inhibitor that is currently known in the art or that will be identified in the future, and includes any chemical entity that, upon administration to a patient, results in inhibition of a biological activity associated with activation of the EGF receptor in the patient, including any of the downstream biological effects otherwise resulting from the binding to EGFR of its natural ligand. Such EGFR kinase inhibitors include any agent that can block EGFR activation or any of the downstream biological effects of EGFR activation that are relevant to treating cancer in a patient. Such an inhibitor can act by binding directly to the intracellular domain of the receptor and inhibiting its kinase activity. Alternatively, such an inhibitor can act by occupying the ligand binding site or a portion thereof of the EGFR receptor, thereby making the receptor inaccessible to its natural ligand so that its normal biological activity is prevented or reduced. Alternatively, such an inhibitor can act by modulating the dimerization of EGFR polypeptides, or interaction of EGFR polypeptide with other proteins, or enhance ubiquitination and endocytotic degradation of EGFR. EGFR kinase inhibitors include but are not limited to low molecular weight inhibitors, antibodies or antibody fragments, antisense constructs, small inhibitory RNAs (i.e. RNA interference by dsRNA; RNAi), and ribozymes. In a preferred embodiment, the EGFR kinase inhibitor is a small organic molecule or an antibody that binds specifically to the human EGFR.

EGFR kinase inhibitors that include, for example quinazoline EGFR kinase inhibitors, pyrido-pyrimidine EGFR kinase inhibitors, pyrimido-pyrimidine EGFR kinase inhibitors, pyrrolo-pyrimidine EGFR kinase inhibitors, pyrazolo-pyrimidine EGFR kinase inhibitors, phenylamino-pyrimidine EGFR kinase inhibitors, oxindole EGFR kinase inhibitors, indolocarbazole EGFR kinase inhibitors, phthalazine EGFR kinase inhibitors, isoflavone EGFR kinase inhibitors, quinalone EGFR kinase inhibitors, and tyrphostin EGFR kinase inhibitors, such as those described in the following patent publications, and all pharmaceutically acceptable salts and solvates of said EGFR kinase inhibitors: International Patent Publication Nos. WO 96/33980, WO 96/30347, WO 97/30034, WO 97/30044, WO 97/38994, WO 97/49688, WO 98/02434, WO 97/38983, WO 95/19774, WO 95/19970, WO 97/13771, WO 98/02437, WO 98/02438, WO 97/32881, WO 98/33798, WO 97/32880, WO 97/3288, WO 97/02266, WO 97/27199, WO 98/07726, WO 97/34895, WO 96/31510, WO 98/14449, WO 98/14450, WO 98/14451, WO 95/09847, WO 97/19065, WO 98/17662, WO 99/35146, WO 99/35132, WO 99/07701, and WO 92/20642; European Patent Application Nos. EP 520722, EP 566226, EP 787772, EP 837063, and EP 682027; U.S. Pat. Nos. 5,747,498, 5,789,427, 5,650,415, and 5,656,643; and German Patent Application No. DE 19629652. Additional non-limiting examples of low molecular weight EGFR kinase inhibitors include any of the EGFR kinase inhibitors described in Traxler, P., 1998, Exp. Opin. Ther. Patents 8(12):1599-1625.

Specific preferred examples of low molecular weight EGFR kinase inhibitors that can be used according to the present invention include [6,7-bis(2-methoxyethoxy)-4-quinazolin-4-yl]-(3-ethynylphenyl) amine (also known as OSI-774, erlotinib, or Tarceva™ (erlotinib HCl); OSI Pharmaceuticals/Genentech/Roche) (U.S. Pat. No. 5,747,498; International Patent Publication No. WO 01/34574, and Moyer, J. D. et al. (1997) Cancer Res. 57:4838-4848); $C_{1-1033}$ (formerly known as PD183805; Pfizer) (Sherwood et al., 1999, Proc. Am. Assoc. Cancer Res. 40:723); PD-158780 (Pfizer); AG-1478 (University of California); CGP-59326 (Novartis); PKI-166 (Novartis); EKB-569 (Wyeth); GW-2016 (also known as GW-572016 or lapatinib ditosylate; GSK); and gefitinib (also known as ZD1839 or Iressa™; Astrazeneca) (Woodburn et al., 1997, Proc. Am. Assoc. Cancer Res. 38:633). A particularly preferred low molecular weight EGFR kinase inhibitor that can be used according to the present invention is [6,7-bis(2-methoxyethoxy)-4-quinazolin-4-yl]-(3-ethynylphenyl) amine (i.e. erlotinib), its hydrochloride salt (i.e. erlotinib HCl, Tarceva™), or other salt forms (e.g. erlotinib mesylate).

Antibody-based EGFR kinase inhibitors include any anti-EGFR antibody or antibody fragment that can partially or completely block EGFR activation by its natural ligand. Non-limiting examples of antibody-based EGFR kinase inhibitors include those described in Modjtahedi, H., et al., 1993, Br. J. Cancer 67:247-253; Teramoto, T., et al., 1996, Cancer 77:639-645; Goldstein et al., 1995, Clin. Cancer Res. 1:1311-1318; Huang, S. M., et al., 1999, Cancer Res. 15:59(8):1935-40; and Yang, X., et al., 1999, Cancer Res. 59:1236-1243. Thus, the EGFR kinase inhibitor can be monoclonal antibody Mab E7.6.3 (Yang, X. D. et al. (1999) Cancer Res. 59:1236-43), or Mab C225 (ATCC Accession No. HB-8508), or an antibody or antibody fragment having the binding specificity thereof. Suitable monoclonal antibody EGFR kinase inhibitors include, but are not limited to, IMC-C225 (also known as cetuximab or Erbitux™; Imclone Systems), ABX-EGF (Abgenix), EMI 72000 (Merck KgaA, Darmstadt), RH3 (York Medical Bioscience Inc.), and MDX-447 (Medarex/Merck KgaA).

Additional antibody-based EGFR kinase inhibitors can be raised according to known methods by administering the appropriate antigen or epitope to a host animal selected, e.g., from pigs, cows, horses, rabbits, goats, sheep, and mice, among others. Various adjuvants known in the art can be used to enhance antibody production.

Although antibodies useful in practicing the invention can be polyclonal, monoclonal antibodies are preferred. Monoclonal antibodies against EGFR can be prepared and isolated using any technique that provides for the production of antibody molecules by continuous cell lines in culture. Techniques for production and isolation include but are not limited to the hybridoma technique originally described by Kohler and Milstein (Nature, 1975, 256: 495-497); the human B-cell hybridoma technique (Kosbor et al., 1983, Immunology Today 4:72; Cote et al., 1983, Proc. Natl. Acad. Sci. USA 80: 2026-2030); and the EBV-hybridoma technique (Cole et al, 1985, Monoclonal Antibodies and Cancer Therapy, Alan R. Liss, Inc., pp. 77-96).

Alternatively, techniques described for the production of single chain antibodies (see, e.g., U.S. Pat. No. 4,946,778) can be adapted to produce anti-EGFR single chain antibodies. Antibody-based EGFR kinase inhibitors useful in practicing the present invention also include anti-EGFR antibody fragments including but not limited to F(ab').sub.2 fragments, which can be generated by pepsin digestion of an intact antibody molecule, and Fab fragments, which can be generated by reducing the disulfide bridges of the F(ab').sub.2 fragments. Alternatively, Fab and/or scFv expression libraries can be constructed (see, e.g., Huse et al., 1989, Science 246: 1275-1281) to allow rapid identification of fragments having the desired specificity to EGFR.

Techniques for the production and isolation of monoclonal antibodies and antibody fragments are well-known in the art, and are described in Harlow and Lane, 1988, Antibodies: A Laboratory Manual, Cold Spring Harbor Laboratory, and in J. W. Goding, 1986, Monoclonal Antibodies: Principles and Practice, Academic Press, London. Humanized anti-EGFR antibodies and antibody fragments can also be prepared according to known techniques such as those described in Vaughn, T. J. et al., 1998, Nature Biotech. 16:535-539 and references cited therein, and such antibodies or fragments thereof are also useful in practicing the present invention.

EGFR kinase inhibitors for use in the present invention can alternatively be based on antisense oligonucleotide constructs. Anti-sense oligonucleotides, including anti-sense RNA molecules and anti-sense DNA molecules, would act to directly block the translation of EGFR mRNA by binding thereto and thus preventing protein translation or increasing mRNA degradation, thus decreasing the level of EGFR kinase protein, and thus activity, in a cell. For example, anti-sense oligonucleotides of at least about 15 bases and complementary to unique regions of the mRNA transcript sequence encoding EGFR can be synthesized, e.g., by conventional phosphodiester techniques and administered by e.g., intravenous injection or infusion. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732).

Small inhibitory RNAs (siRNAs) can also function as EGFR kinase inhibitors for use in the present invention. EGFR gene expression can be reduced by contacting the tumor, subject or cell with a small double stranded RNA (dsRNA), or a vector or construct causing the production of a small double stranded RNA, such that expression of EGFR is specifically inhibited (i.e. RNA interference or RNAi). Methods for selecting an appropriate dsRNA or dsRNA-encoding vector are well known in the art for genes whose sequence is known (e.g. see Tuschi, T., et al. (1999) Genes Dev. 13(24): 3191-3197; Elbashir, S. M. et al. (2001) Nature 411:494-498; Hannon, G. J. (2002) Nature 418:244-251; McManus, M. T. and Sharp, P. A. (2002) Nature Reviews Genetics 3:737-747; Bremmelkamp, T. R. et al. (2002) Science 296:550-553; U.S. Pat. Nos. 6,573,099 and 6,506,559; and International Patent Publication Nos. WO 01/36646, WO 99/32619, and WO 01/68836).

Ribozymes can also function as EGFR kinase inhibitors for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hammerhead motif ribozyme molecules that specifically and efficiently catalyze endonucleolytic cleavage of EGFR mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Both antisense oligonucleotides and ribozymes useful as EGFR kinase inhibitors can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

The invention also encompasses a pharmaceutical composition that is comprised of an EGFR kinase inhibitor and cisplatin combination in combination with a pharmaceutically acceptable carrier.

Preferably the composition is comprised of a pharmaceutically acceptable carrier and a non-toxic therapeutically effective amount of an EGFR kinase inhibitor compound and cisplatin combination (including pharmaceutically acceptable salts of each component thereof).

Moreover, within this preferred embodiment, the invention encompasses a pharmaceutical composition for the treatment of disease, the use of which results in the inhibition of growth of neoplastic cells, benign or malignant tumors, or metastases, comprising a pharmaceutically acceptable carrier and a non-toxic therapeutically effective amount of an EGFR kinase inhibitor compound and cisplatin combination (including pharmaceutically acceptable salts of each component thereof).

The term "pharmaceutically acceptable salts" refers to salts prepared from pharmaceutically acceptable non-toxic bases or acids. When a compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (cupric and cuprous), ferric, ferrous, lithium, magnesium, manganese (manganic and manganous), potassium, sodium, zinc and the like salts. Particularly preferred are the ammonium, calcium, magnesium, potassium and sodium slats. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylameine, trimethylamine, tripropylamine, tromethamine and the like.

When a compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric and tartaric acids.

The pharmaceutical compositions of the present invention comprise an EGFR kinase inhibitor compound and cisplatin combination (including pharmaceutically acceptable salts of each component thereof) as active ingredient, a pharmaceutically acceptable carrier and optionally other therapeutic ingredients or adjuvants. Other therapeutic agents may include those cytotoxic, chemotherapeutic or anti-cancer agents, or agents which enhance the effects of such agents, as listed above. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds represented by an EGFR kinase inhibitor compound and cisplatin combination (including pharmaceutically acceptable salts of each component thereof) of this invention can be combined as the active ingredient in intimate admixture with a pharmaceutical carrier according to conventional pharmaceutical compounding techniques. The carrier may take a wide variety of forms depending on the form of preparation desired for administration, e.g. oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a nonaqueous liquid, as an oil-in-water emulsion, or as a water-in-oil liquid emulsion. In addition to the common dosage forms set out above, an EGFR kinase inhibitor compound and cisplatin combination (including pharmaceutically acceptable salts of each component thereof) may also be administered by controlled release means and/or delivery devices. The combination compositions may be prepared by any of the methods of pharmacy. In general, such methods include a step of bringing into association the active ingredients with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and an EGFR kinase inhibitor compound and cisplatin combination (including pharmaceutically acceptable salts of each component thereof). An EGFR kinase inhibitor compound and cisplatin combination (including pharmaceutically acceptable salts of each component thereof), can also be included in pharmaceutical compositions in combination with one or more other therapeutically active compounds. Other therapeutically active compounds may include those cytotoxic, chemotherapeutic or anti-cancer agents, or agents which enhance the effects of such agents, as listed above.

Thus in one embodiment of this invention, a pharmaceutical composition can comprise an EGFR kinase inhibitor compound and cisplatin in combination with an anticancer agent, wherein said anti-cancer agent is a member selected from the group consisting of alkylating drugs, antimetabolites, microtubule inhibitors, podophyllotoxins, antibiotics, nitrosoureas, hormone therapies, kinase inhibitors, activators of tumor cell apoptosis, and antiangiogenic agents.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient.

For example, a formulation intended for the oral administration to humans may contain from about 0.5 mg to about 5 g of active agent, compounded with an appropriate and convenient amount of carrier material that may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical sue such as, for example, an aerosol, cream, ointment, lotion, dusting powder, or the like.

Further, the compositions can be in a form suitable for use in transdermal devices. These formulations may be prepared, utilizing an EGFR kinase inhibitor compound and cisplatin combination (including pharmaceutically acceptable salts of each component thereof) of this invention, via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing an EGFR kinase inhibitor compound and cisplatin combination (including pharmaceutically acceptable salts of each component thereof) may also be prepared in powder or liquid concentrate form.

Dosage levels for the compounds of the combination of this invention will be approximately as described herein, or as described in the art for these compounds. It is understood, however, that the specific dose level for any particular patient will depend upon a variety of factors including the age, body weight, general health, sex, diet, time of administration, route of administration, rate of excretion, drug combination and the severity of the particular disease undergoing therapy.

This invention will be better understood from the Experimental Details that follow. However, one skilled in the art will readily appreciate that the specific methods and results discussed are merely illustrative of the invention as described more fully in the claims which follow thereafter, and are not to be considered in any way limited thereto.

Experimental Details:
Introduction

The cancer cell-specific epidermal growth factor receptor (HER1/EGFR) is a valuable molecular target in cancer therapy (Ciardiello, F and Tortora G. (2002) Expert Opin. Investig. Drugs 11:755-768). Many cancers over-express HER1/EGFR: head and neck squamous cell carcinoma (70-100%), non-small cell lung cancer (NSCLC) (50-90%), prostate cancer (40-70%), glioma (10-50%), gastric cancer (30-60%), breast cancer (35-70%), colorectal cancer (45-80%), pancreatic cancer (30-50%) and ovarian cancer (35-60%) (Ciardiello, F and Tortora G. (2002) Expert Opin. Investig. Drugs 11:755-768); Salomon D. S., et al. (1995) Crit. Rev. Oncol. Hematol. 19:183-232). Salomon et al also highlighted the link between over-expressed HER1/EGFR and patients with advanced disease, metastases and poor prognosis.

NSCLC is the most common lung cancer. According to the extent of the disease, the treatment approach will differ. For early stage of the disease, surgery is the only cure, and a multimodal approach with chemo/radio therapy can be associated with improved outcome. In advanced disease, chemotherapy is the main option, which offers small improvements in overall survival. Thus, the medical need remains high in NSCLC with the search for more effective and better tolerated regimens. Many traditional cytotoxics have been used as monotherapy in NSCLC, including vindesine, carboplatin, etoposide, ifosfamide, cyclophosphamide, vincristine, and mitomycin and cisplatin (Rajkumar S. V., and Adjei A A. (1998) Cancer Treat Rev. 24:35-53). Monotherapy with these drugs produces only small improvement, but combination therapy with cisplatin has lessened patients' illness and improved their quality of life in randomised trials (Bunn P. A. Jr, and Kelly K. (1998) Clin Cancer Res. 4(5):1087-1100).

Gemcitabine was developed in the 1990s, and inhibits ribonuclease reductase. Gemcitabine monotherapy has a greater probability of tumor response and improved patient quality of life (in terms of reduced hair loss, nausea and vomiting, and appetite loss) than standard cisplatin/etoposide chemotherapy (ten Bokkel W. W., et al. (1999) Lung Cancer 26(2): 85-94).

Combination trials by the European Organization for Research and Treatment of Cancer (EORTC) compared cisplatin and teniposide to cisplatin and paclitaxel (Giaccone G, et al. (1998) J. Clin. Oncol. 16:2133-2141). As the latter combination gave better palliation for advanced NSCLC (even though a clear survival benefit was not met), it has been recommended as one of the standard of care for advanced NSCLC patients. In addition, a combination of gemcitabine and cisplatin has been shown to act synergistically in vitro and at least additively in vivo (Peters G. J. et al. (1995) Semin. Oncol. 22(4 Suppl. 11):72-79). In phase II trials, the response rate for gemcitabine and cisplatin was 47% and median survival 57 weeks, with a 1-year survival rate of 48% (Bunn P. A. Jr, and Kelly K. (1998) Clin Cancer Res. 4(5):1087-1100).

New treatments for cancer take a cancer-cell specific approach, and promise less toxicity than the older cytotoxic drugs. As cancer cell-specific targets are only part of the disease aetiology, treatments combining targeted and conventional drugs may have a synergistic effect. Optimal treatment of NSCLC is likely to consist of EGFR inhibitors in combination with traditional chemotherapy.

Erlotinib (Tarceva™, OSI-774) is a selective, orally available small-molecule inhibitor of the HER1/EGFR tyrosine-kinase domain. It has potent antitumour activity in preclinical animal models of head and neck and vulval carcinoma (Pollack V. A., et al. (1999) J. Pharmacol. Exp. Ther. 291:739-48). Erlotinib induces apoptosis in vitro and is active against various EGFR-expressing human tumour xenografts in vivo (Moyer J. D. et al. (1997) Cancer Res. 57:4838-4848). In an open-label, phase II study of NSCLC patients who had failed platinum-based chemotherapy (Perez-Soler R. et al. (2001) Proc. Am. Soc. Clin. Oncol. 20:310a (Abstract 1235)), erlotinib had encouraging anticancer activity.

In this study we investigated whether combining erlotinib with cisplatin or gemcitabine in athymic nude mice bearing NSCLC xenograft models acts synergistically or antagonistically in inhibiting tumour growth. The H460a and A549 NSCLC tumour models were chosen because they clearly express EGFR, with around 70,000-80,000 binding sites per cell (Bianco, C. et al. (2002) Clin. Cancer Res. 8(10):3250-3258; Lee, M. et al. (1992) J. Natl. Cancer Inst. Monogr. (13):117-123). A549 is slow growing and H460a is more aggressive and faster growing.

Materials and Methods
Animals

Female, athymic, nu/nu-nuBR nude mice (Charles River Labs, Wilmington, USA) of around 10-12 weeks and weighing 23-25 g were used. The health of the mice was assessed daily by observation and analysis of blood samples taken from sentinel animals on the shared shelf racks. All animals were allowed to acclimatise and recover from shipping-related stress for 1 week.

Autoclaved water and irradiated food (5058-ms Pico Lab [mouse] breed chow, Purina Mills, Richmond, Ind.) were provided ad libitum, and the animals were kept in a 12-hour light and dark cycle. Cages, bedding and water bottles were autoclaved before use and changed weekly. All animal experiments were in accordance with protocols approved by the Roche Animal Care and Use Committee.

Cell Culture and Animal Studies

H460a cells (provided by Dr Jack Roth, MD, Anderson) were grown in Dulbecco's Modified Eagle Media (DMEM) supplemented with 10% Foetal Bovine Serum (FBS). A549 cells (American Type Culture Collection [Manassas, Va.] were grown in Roswell Park Memorial Institute medium (RPMI) 1640+10% FBS. The cell concentrations for implant were $1\times10^7$ cells/0.2 mL for H460a and $7.5\times10^6$ cells/0.2 mL for A549.

Cells were suspended in phosphate-buffered saline, and implanted subcutaneously in the right flank of each mouse. Once palpable tumours were established, animals were randomised so that all groups had similar starting mean tumour volumes of 100-150 mm$^3$. Tumour measurements and mouse weights were taken three times per week. Animals were individually monitored throughout the experiment.

Test Agents and Drug Treatment.

Erlotinib (OSI Pharmaceuticals, Uniondale, N.Y.) was formulated as a fine suspension with sodium carboxymethylcellulose and Tween 80 in water for injection. Erlotinib (0.2 mL/animal) was given orally using a 1 mL syringe and 18-gauge gavage needle. All groups were treated daily for 3 weeks.

Cisplatin (Platinol-AQ™, Bristol-Myers Squibb) was provided in a stock sterile saline solution of 1 mg/mL. An aliquot of the stock vial solutions was taken for each dose group, consisting of the drug needed for the entire study, and diluted further with sterile saline, to give a solution of 0.5 mL dosing volume for each animal. Cisplatin was given intraperitoneally using a 3 mL syringe and 26-gauge needle. All groups were treated every 6 days for 3 weeks (a total of three injections).

Calculations and Statistical Analysis.

Weight loss was calculated as percent change in mean group body weight, using the formula:

$$((W-W_0)/W_0)\times 100$$

where 'W' represents mean body weight of the treated group at a particular day, and '$W_0$' represents mean body weight of the same group at start of treatment. Maximum weight loss was also calculated using the above formula, giving the maximum percentage of body weight lost at any time in the entire experiment for a particular group. Treatment efficacy was assessed by tumor growth inhibition. Tumour volumes of treated groups were given as percentages of tumor volumes of the control groups (% T/C), using the formula:

$$100\times((T-T_0)/(C-C_0))$$

where 'T' represents mean tumor volume of a treated group on a specific day during the experiment, '$T_0$' represented mean tumor volume of the same group on the first day of treatment, C represents mean tumor volume of a control group on a particular day of the experiment, and $C_0$ represents mean tumor volume of the same group on the first day of treatment.

Tumor growth inhibition was calculated using the formula:

$$100-\%\ T/C$$

Tumor volume (mm$^3$) was calculated using the ellipsoid formula:

$$(D\times(d^2))/2$$

where 'D' represents the large diameter of the tumor, and 'd' represents the small diameter. In some cases, tumor regression and/or percentage change in tumor volume was calculated using the formula:

$$((T-T_0)/T_0)\times 100$$

where 'T' represents mean tumor volume of the treated group at a particular day, and '$T_0$' represents mean tumor volume of the same treated group at the start of treatment.

Statistical analysis was by the rank sum test and one-way analysis of variance (ANOVA) and a post-hoc Bonferroni t-test (SigmaStat, version 2.03, Jandel Scientific, San Francisco, Calif.). The significance level was set at p 0.05.

Pharmacokinetic Analysis

For single-dose pharmacokinetics (PK), blood samples from three mice per time point were collected by cardiac puncture at 5, 15, 30, 60 minutes and 2, 4, 8, 16, 24 hours post-dose. For chronically treated animals, blood samples from two or three mice per time point were collected via the retro-orbital sinus at 1 and 6 hours. Collection tubes contained ethylene diamine tetra-acetic acid (EDTA) as anticoagulant. Samples were stored at −70° C. Plasma concentrations of erlotinib were determined using a liquid chromatography and tandem mass spectrometry (LC-MS/MS) method with quantification limits of 1 ng/mL. PK parameters were estimated by non-compartmental analysis of the composite data, using the PK evaluation programme WinNonlin PRO® version 3.1 (Pharsight Inc). In one study, erlotinib tumor (H460a) concentrations were determined using a selective LC-MS/MS method with a quantification limit of 1 ng/g tissue.

Pathology/Necropsy

Five mice per treatment from all remaining groups were given a full necropsy at the end of the study. Whole blood was also collected from these mice for haematology and clinical chemistry.

Tumor samples were fixed by immersion in 10% zinc formalin then processed in a Tissue-Tek® VIP (Sakura) and embedded in paraffin. Sections for immunohistochemistry were cut at 5µ. Pre-immune rabbit or goat serum (Dako Ltd) was used as the negative control. Sections were immersed in Target Retrieval Solution (Dako Ltd) and heated to 94° C. in a steamer (Black & Decker) for 20 minutes. Endogenous peroxidase activity was quenched with 6% $H_2O_2$ in methanol for 15 minutes.

To block non-specific tissue-binding sites, sections were blocked by 10% normal serum from the species in which the secondary antibody was raised. Sections were incubated for 20 minutes at room temperature in serum prepared in Ultra-V (Lab Vision).

For platelet endothelial cell adhesion molecule (PECAM-1, CD31) antigen and EGFR antigen, the sections were incubated overnight at room temperature with a polyclonal goat anti-PECAM-1 IgG (Santa Cruz Biotechnology, Santa Cruz, Calif.) diluted 1:800 in Antibody Diluent (Dako Ltd) or with a polyclonal rabbit anti-EGFR IgG (BioGenex, San Ramon, Calif.) diluted 1:50 in Antibody Diluent (Dako Ltd). Sections were incubated with Vectastain Elite ABC-peroxidase (Vector Laboratories) for 45 minutes at room temperature.

For the Ki-67 antigen, sections were incubated for 1 hour at room temperature with a polyclonal anti Ki-67 IgG (NeoMarkers, Fremont, Calif.) diluted 1:2,000 in Antibody Diluent (Dako Ltd), followed by the addition of horseradish peroxidase-labelled strepavidin complex for 30 minutes.

To detect apoptosis, the TUNEL TdT-FragEL™ DNA fragmentation detection kit (Oncogene Research Products, San Diego, Calif.) was used according to the manufacturer's recommendations. For all four antigens, Vector Nova Red (Vector Laboratories) was the final chromogen and haematoxylin the nuclear counterstain.

Results and Discussion

Results

EGFR Immunohistochemical Staining in NSCLC Xenografts

The EGFR expression pattern in the H460a and A549 tumors was examined by immunohistochemistry. Both cell lines had a similar membranous pattern of staining for EGFR (data not shown). This confirms past results showing equivalent expression of EGFR in these two tumor lines (Bianco, C. et al. (2002) Clin. Cancer Res. 8(10):3250-3258; Lee, M. et al. (1992) J. Natl. Cancer Inst. Monogr. (13):117-123).

Single and Chronic-Dose PK Assessment of Erlotinib in Athymic Nude Mice

In Non-Tumor Bearing Mice.

Erlotinib 20 and 100 mg/kg was given by gavage to female nu/nu athymic mice. The doses refer to the hydrochloride salt with an active drug (free base) content of 91.5%. The formulations were sodium carboxymethylcellulose suspensions containing 2.5 mg/mL and 12.5 mg/mL of erlotinib, respectively. Three animals per time point were evaluated for PK data (FIG. 3).

The mice given 100 mg/kg had high systemic exposures to erlotinib, with an $AUC_{last}$ value of approximately 196,000 h*ng/mL. The $AUC_{last}$ following 20 mg/kg was 33,500 h*ng/mL. The exposure (AUC) was dose-proportional. Mean maximum plasma concentrations were approximately 24,000 ng/mL after 100 mg/kg, and 9,100 ng/mL after 20 mg/kg. Maximum plasma concentration was 0.5-1.0 hours post dose. Mean apparent terminal half-life was about 4 hours and the average mean residence time about 7 hours.

In Tumor-Bearing Mice.

After erlotinib 6.3, 12.5, 25.0, 100.0, and 150.0 mg/kg was given orally to nu/nu athymic mice, plasma concentration was up to 16,700 ng/mL and 8,870 ng/mL at 1 hour and 6 hours post dose, respectively (FIG. 1a). The respective mean tumor concentrations following oral doses of 150 mg/kg, sampled at the same time points as the plasma samples, were 4,800 and 3,090 ng/g tissue.

Inter-individual variability of the plasma concentrations was moderate, with a relative standard deviation (RSD) of about 35-40% (range: 5.2-120%). The exposure was dose-dependent and more than dose-proportional with ascending doses. Tumor concentrations also correlated well with plasma concentrations in this study (FIG. 1b).

Determination of Maximum Tolerated Doses (MTD) in Athymic Nude Mice.

Erlotinib MTD

The MTD for erlotinib was 100 mg/kg (FIG. 5). Mice showing signs of toxicity all had similar lesions. Gross toxicity was found in the skin and gastro-intestinal tract. One mouse in the 400 mg/kg group died. The rest of the animals in this group were euthanized because of morbidity. Mice given 200 mg/kg had marked weight loss and all were euthanized. Our previous efficacy studies have shown, however, that erlotinib 150 mg/kg in this formulation is also well tolerated for 3 weeks (authors, unpublished observation).

Cisplatin MTD

The MTD in this study was 6 mg/kg every 6 days×3 i.p. (Table 2). There are reports of various MTDs in mice for cisplatin, using either the i.p. or intravenous (i.v.) route, including 4 mg/kg every 6 days×2 i.v. in nude mice (Perez-Soler R. et al. (2001) Proc. Am. Soc. Clin. Oncol. 20:310a (Abstract 1235)), 6 mg/kg every 6 days×3 i.p. in C57/B16 mice (van Moorsel C. J., et al. (1999) Eur. J. Cancer 35(5): 808-814) and 4 mg/kg every 4 days×3 i.v. in nude mice (Riccardi, A., (2001) Cancer Chemother. Pharmacol. 47(6): 498-504).

Mice were given cisplatin i.p. in increasing doses from 3 mg/kg to 12 mg/kg. The classic toxic side effects of cisplatin therapy are renal, gastro-intestinal, and neurological (Perez-Soler R. et al. (2001) Proc. Am. Soc. Clin. Oncol. 20:310a (Abstract 1235). Mice in both groups (to a lesser extent in the 9 mg/kg group) had clear signs of gastro-intestinal toxicity. A complete necropsy was not done, therefore it is not known if there were histologic lesions in the kidneys, central nervous system, or gastro-intestinal tract in these mice, or in those in lower dose groups. But there were no gross signs of nephrotoxicity, or behavioural or postural signs of neurotoxicity in any dose group.

Effects of Erlotinib on Established NSCLC Xenografts.

Dose Response Study in H460a.

At the end of the study in the H460a NSCLC xenograft (day 28 post tumor implantation), erlotinib, as a monotherapy, had significant dose-dependent efficacy. In the 100 mg/kg group there was growth inhibition of 61% ($p \leq 0.001$ versus vehicle control).

Figure 2:
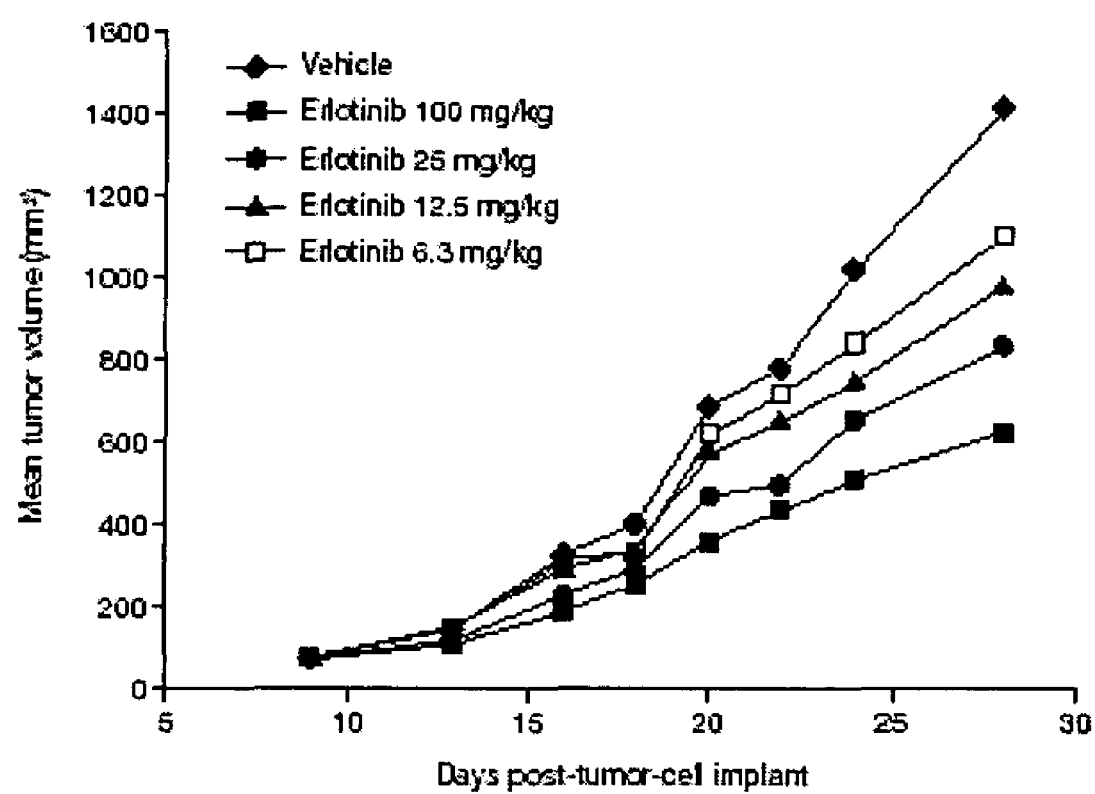
FIG. 2: Effect of erlotinib on mean tumor volume in H460a NSCLC xenograft model. Mice were implanted with H460a NSCLC cells. When palpable tumors were established, animals were randomized such that each group had a mean starting tumor volume of 100-150 mm$^3$. Mice were given daily oral doses of erlotinib at 0, 6.3, 12.5, 25 or 100 mg/kg for 21 days. Tumor size was measured 3 times per week. Values are means, n=10.

The other groups had the following growth inhibition: 25 mg/kg: 46% ($p \leq 0.001$ versus vehicle control); 12.5 mg/kg: 36% (p=0.003 versus vehicle control); 6.25 mg/kg: 28% (p=0.014 versus vehicle control) (FIG. 2). There were no partial or complete regressions.

Combination Activity of Erlotinib and Cisplatin in H460a.

Figure 4:
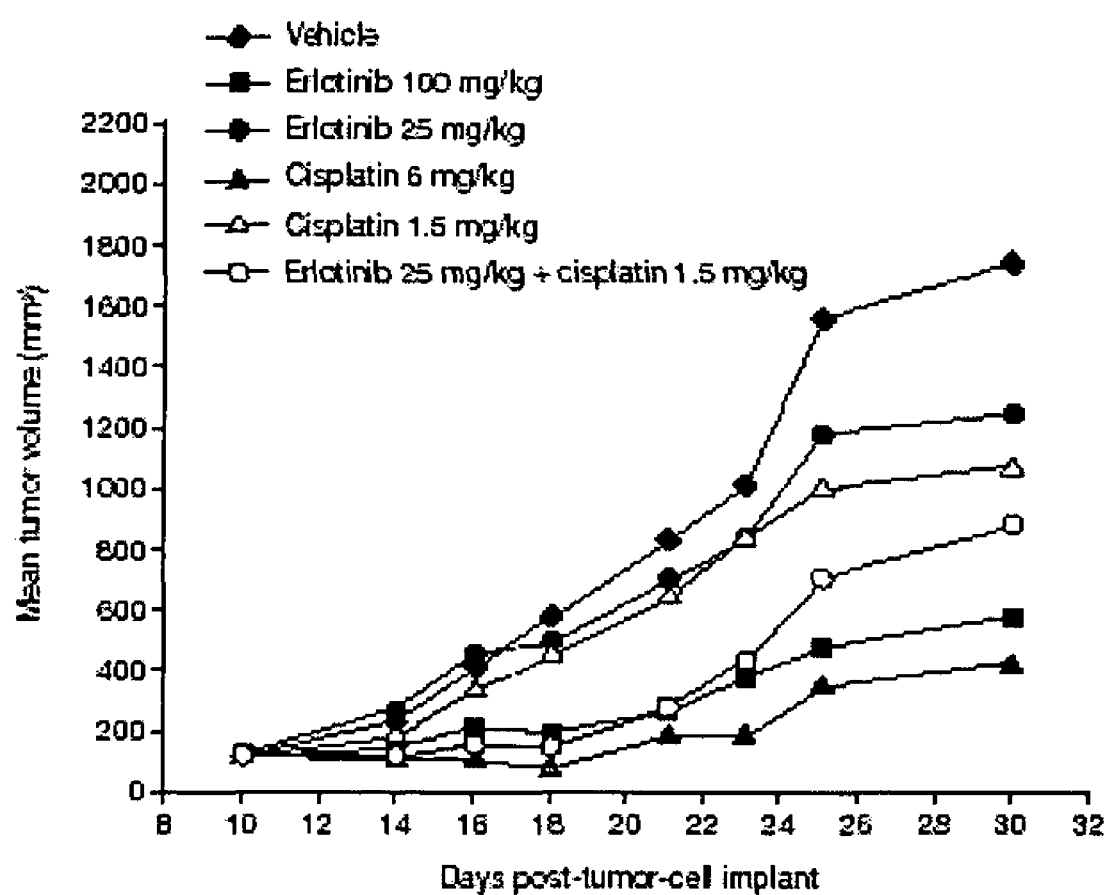
FIG. 4: Effect of erlotinib and cisplatin alone and in combination on mean tumor volume in the H460a NSCLC xenograft model. Mice were implanted with H460a NSCLC cells. When palpable tumors were established, animals were randomised such that each group had a mean starting tumor volume of 100-1150 mm$^3$. Mice were treated with vehicle, oral erlotinib alone at 25 or 100 mg/kg/day for 3 weeks, i.p. cisplatin alone at 1.5 or 6 mg/kg every 6 days for 3 weeks, or erlotinib at 25 mg/kg/day with cisplatin at 1.5 mg/kg every 6 days. Tumor size was measured 3 times per week. Values are means, n=10.

Cisplatin 6 mg/kg significantly inhibited tumor growth by 81% ($p \leq 0.001$) (FIG. 4). Cisplatin 1.5 mg/kg inhibited tumor growth by 42% (p=0.014). Combined cisplatin 6 mg/kg and erlotinib 100 mg/kg was lethal, with signs of toxicity at day 5 post tumor implantation. All mice were dead by day 23 post tumor implantation (treatment day 13).

Combined cisplatin 1.5 mg/kg and erlotinib 25 mg/kg was well tolerated and inhibited tumor growth by 53% (p=0.003 versus vehicle). There were no partial or complete regressions. This tumor growth inhibition was not additive as it was not significantly better than either cisplatin or erlotinib administered at 25% of the MTD. This combination was also not significantly better than erlotinib 100 mg/kg or cisplatin 120 mg/kg.

Combination Activity Erlotinib and Cisplatin in A549.

Figure 6:
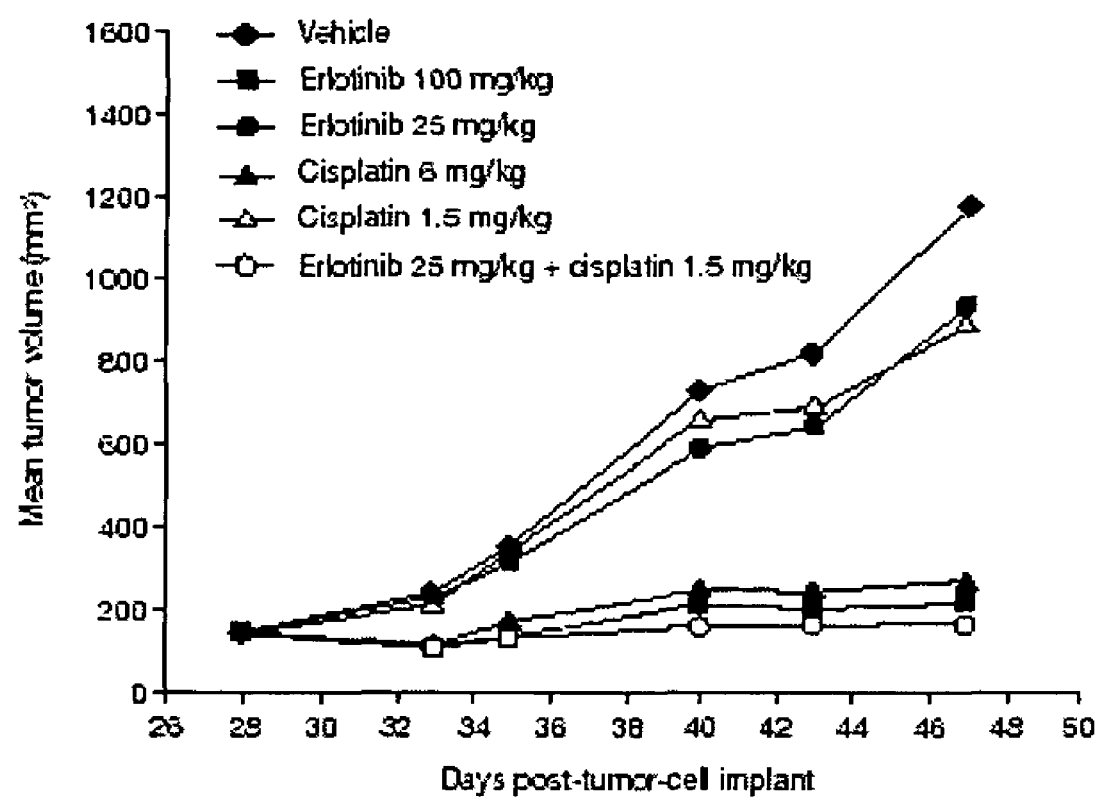
FIG. 6: Effect of erlotinib and cisplatin alone and in combination on mean tumor volume in the A549 NSCLC xenograft model. Mice were implanted with A549 NSCLC cells. When palpable tumors were established, animals were randomised such that each group had a mean starting tumor volume of 100-150 mm$^3$. Mice were treated with vehicle, oral erlotinib alone at 25 or 100 mg/kg/day for 3 weeks, i.p. cisplatin alone at 1.5 or 6 mg/kg every 6 days for 3 weeks, or erlotinib at 25 mg/kg/day with cisplatin at 1.5 mg/kg every 6 days. Tumor size was measured 3 times per week. Values are means, n=10.

At the end of this study (day 47 post tumor implantation, treatment day 19), erlotinib 100 mg/kg significantly inhibited tumor growth by 93% ($p \leq 0.001$) (FIG. 6). There was one partial regression (2%). Erlotinib 25 mg/kg inhibited tumor growth by 25%. Cisplatin 6 mg/kg significantly inhibited tumor growth by 88% ($p \leq 0.001$) with one partial regression (2%). Cisplatin 1.5 mg/kg inhibited tumor growth by 30%, although this was non-significant.

Because of toxicities in previous studies, cisplatin and erlotinib were not combined at the high doses. Combined cisplatin 1.5 mg/kg and erlotinib 25 mg/kg were well tolerated by all mice, with no significant weight loss or overall signs of toxicity. This combination significantly inhibited tumor growth by 98% ($p \leq 0.001$ versus vehicle control), with five partial regressions (range: 2%-28%). This tumor growth inhibition was synergistic, as it was significantly better than either cisplatin ($p \leq 0.05$) or erlotinib ($p \leq 0.05$) given at 25% of the MTD. This combination was not significantly better than erlotinib 100 mg/kg, and cisplatin 6 mg/kg.

Treatment-Related Effects on Normal and Tumor Tissue.

Necropsy in Animals Given Monotherapy.

Figure 7:
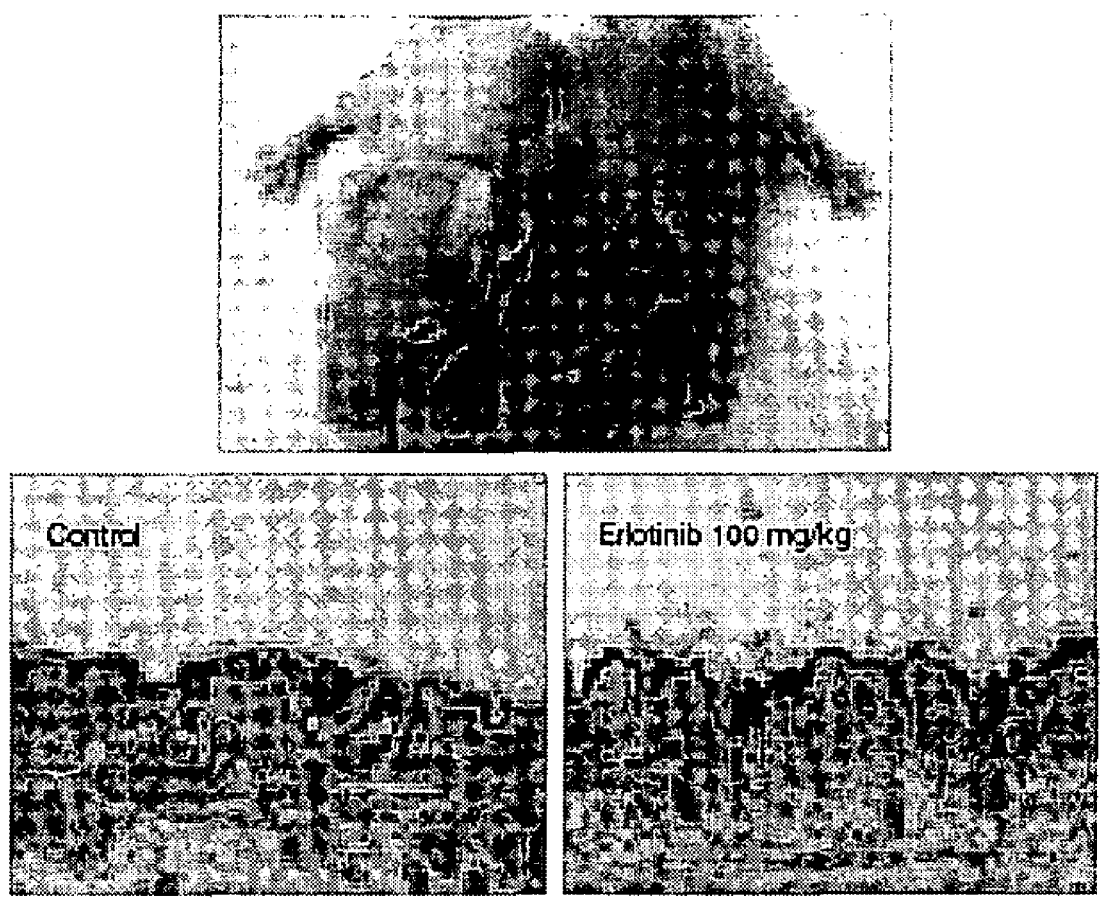
FIG. 7: Skin lesions in mice administered erlotinib. At necropsy, skin samples were fixed in 10% buffered formalin, embedded in paraffin, sectioned at 5µ and stained with haematoxylin and eosin. In mice given erlotinib at 100 mg/kg/day for 21 days, skin lesions were grossly characterised as reddened and flaky. Histologically the lesions consisted of diffuse, mild to moderate epidermal acanthosis, epidermal hyperkeratosis, focal escharosis, and infiltration of mostly acute inflammatory cells in the dermis. The lesions were transient and dissipated with continued treatment.
Figure 8:
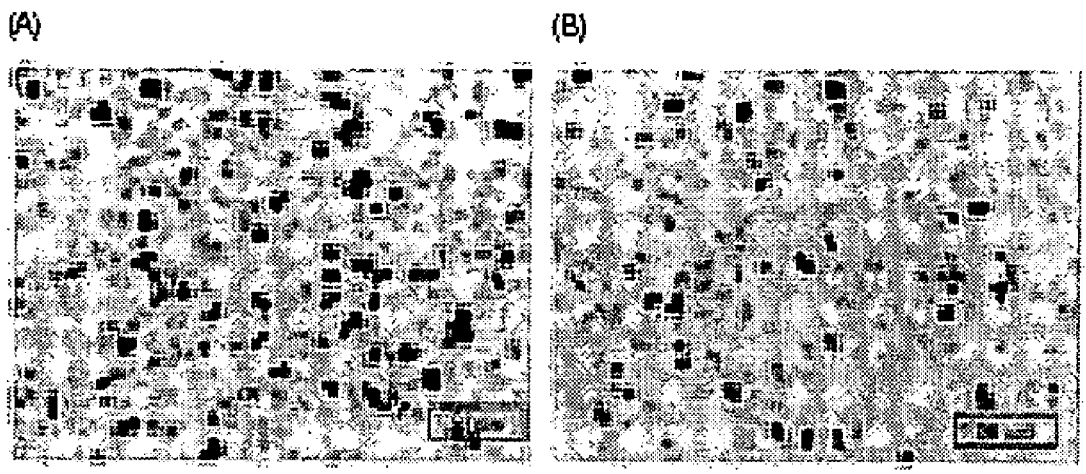
FIG. 8: Photomicrographs of immunohistochemical staining of NSCLC in xenograft models. Sections of tumors from nude mice were stained for the antigen Ki67 to detect cell proliferation in control mice (A) and mice treated with erlotinib at 100 mg/kg/day for 21 days (B). Dark areas represent Ki67 staining indicative of proliferative activity.

In animals given erlotinib monotherapy, there were no changes in haematology parameters or clinical chemistry parameters (data not shown). There were treatment-related macroscopic changes in the skin. The mice had substantial reddening and crusting of the skin of the muzzle (FIG. 7) that might have been due to the high level of expression of EGFR in the skin. These lesions were transient and dissipated with continued treatment. Treatment-related anti-tumor effects consisted of a mild decrease in Ki-67 proliferative index in the erlotinib 1000 mg/kg in both NSCLC xenograft tumor models (FIG. 8). There was no significant difference in the frequency of apoptosis in tumor cells in the treated xenografts, and no clear effect on angiogenesis as measured by microvascular density (MVD) via immunohistochemical staining for the endothelial cell marker, CD31.

Necropsy in Animals Given Erlotinib/Cisplatin Combination.

Severity of microscopic lesions was dose dependent in the kidneys of groups given cisplatin alone and in combination. The primary lesions were tubular necrosis and tubular basophilia (data not shown). Treatment-related effects on haematology and serum chemistry parameters were minimal. Cisplatin is a nephrotoxin, producing proximal and distal tubular cell injury (Klaassen, and Curtis, D., (Editor). Casarett and Doull's Toxicology: The Basic Science of Poisons. 6th Ed. McGraw-Hill, New York (2001), pp. 399-401, 496, 497, 500, 503, 506, 511, 695, 852 and 853). Based on the pathology data, the combination of erlotinib 25 mg/kg and cisplatin 1.5 mg/kg also had clear antineoplastic effects, and again, toxicity did not appear to be increased. Effects on tumor cell proliferation in the combination group were similar to those of high-dose erlotinib monotherapy (FIG. 8b).

Discussion

These results show that erlotinib, a potent, orally available and selective small-molecule inhibitor of HER1/EGFR, has strong antitumor activity in human NSCLC xenograft models expressing similar numbers of HER1/EGFR, as monotherapy and in combination with conventional chemotherapeutics.

In the xenograft model H460a, it had an excellent dose-response relationship, and tumor concentration correlated well with plasma concentration.

The two human NSCLC cell lines, when grown as subcutaneous tumors in athymic mice, had different tumor growth kinetics, with a doubling time of 5 days for H460a and 10 days for A549. Erlotinib monotherapy at 100 mg/kg significantly inhibited tumor growth in the H460a xenograft model.

There was significant tumor-growth inhibition and partial remission with the cisplatin/erlotinib combination, administered at 25% of the MTD, in the slow-growing A549 tumor (90%). Tumor growth inhibition with erlotinib in combination with cisplatin was significantly increased compared with erlotinib monotherapy ($p \leq 0.05$). In the faster-growing H460a tumor, there was substantial tumor growth inhibition with the cisplatin/erlotinib combination (53%) using a quarter of the MTD of either of the compounds. However, tumor growth inhibition with this combination was not significantly different from that with monotherapy. A549 is slow growing and therefore assumed to be more dependent on angiogenesis. Erlotinib is thought to be an indirect anti-angiogenic agent (Kerbel, R, and Folkman, J. (2002) Nat. Rev. Cancer 2(10): 727-39), so it is not surprising that it has greater efficacy against A549. Erlotinib inhibits the binding of adenosine triphosphate (ATP) to the intracellular tyrosine kinase domain of HER1/EGFR, blocking receptor phosphorylation and associated downstream signalling (Moyer J. D. et al. (1997) Cancer Res. 57:4838-4848). The result is inhibition of cellular processes associated with tumor growth and progression, such as proliferation, angiogenesis, metastasis and protection from apoptosis (Moyer J. D. et al. (1997) Cancer Res. 57:4838-4848). Unfortunately, anti-angiogenic effects were not detected by MVD in the tumors treated with erlotinib, possibly because the assay was not sensitive enough.

In both NSCLC models, cisplatin (1.5 mg/kg) with erlotinib (25 mg/kg), administered at a quarter of the MTD, were well tolerated, with no or insignificant weight loss, suggesting potential significant quality of life benefits for patients, by maintaining efficacy with less risk of side effects. In contrast, the high-dose combination of erlotinib and conventional agents at their individual maximum tolerated doses was not tolerated. This may be related to the fact that supportive care cannot be used preclinically.

Phase III trials of erlotinib in combination with gemcitabine and cisplatin, or with carboplatin and paclitaxel in humans with NSCLC have been disappointing since a conclusive survival benefit was not demonstrated. Nevertheless, the preclinical studies reported here have clearly shown that erlotinib in combination with cisplatin has an additive effect on inhibiting tumor growth. These findings support the need for further examination of the effects of erlotinib in various clinical settings such as its sequential use with other chemotherapy agents, and in selected patient populations. In addition, HER1/EGFR is over expressed in numerous cancers, including head and neck, prostate, glioma, gastric, breast, cervical, pancreatic and ovarian cancer (Ciardiello, F and Tortora G. (2002) Expert Opin. Investig. Drugs 11:755-768); Salomon D S, et al. (1995) Crit. Rev. Oncol. Hematol. 19:183-232). Therefore, erlotinib in combination with cisplatin may have efficacy benefits in other cancers with HER1/EGFR-expressing solid-cell tumors.

In conclusion, in NSCLC, the antitumor activity of erlotinib in xenograft tumors with similar levels of EGFR expression is robust both as monotherapy and in combination with cisplatin. Further research is needed to fully evaluate this promising new avenue in cancer treatment.

Incorporation by Reference

All patents, published patent applications and other references disclosed herein are hereby expressly incorporated herein by reference.

EQUIVALENTS

Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A method for the treatment of non-small cell lung cancer (NSCLC), comprising administering to a subject in need of such treatment (i) a sub-therapeutic first amount of the EGFR kinase inhibitor erlotinib, or a pharmaceutically acceptable salt thereof; and (ii) a sub-therapeutic second amount of cisplatin.

2. A method for treating non-small cell lung cancer (NSCLC) tumors or non-small cell lung cancer (NSCLC) tumor metastases in a patient, consisting of administering to said patient simultaneously or sequentially a therapeutically effective amount of the EGFR kinase inhibitor erlotinib and cisplatin, and one or more pharmaceutical carriers.

* * * * *